(12) United States Patent
Watanabe

(10) Patent No.: US 11,399,805 B2
(45) Date of Patent: Aug. 2, 2022

(54) ULTRASOUND DIAGNOSTIC DEVICE AND ULTRASOUND SIGNAL PROCESSING METHOD

(71) Applicant: Konica Minolta, Inc., Tokyo (JP)

(72) Inventor: Yasuhito Watanabe, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 397 days.

(21) Appl. No.: 15/612,295

(22) Filed: Jun. 2, 2017

(65) Prior Publication Data
US 2017/0347990 A1 Dec. 7, 2017

(30) Foreign Application Priority Data
Jun. 6, 2016 (JP) .............................. JP2016-112802

(51) Int. Cl.
*A61B 8/08* (2006.01)
*A61B 8/00* (2006.01)
*G01S 7/52* (2006.01)

(52) U.S. Cl.
CPC .............. *A61B 8/485* (2013.01); *A61B 8/461* (2013.01); *A61B 8/5223* (2013.01); *A61B 8/54* (2013.01); *G01S 7/52022* (2013.01)

(58) Field of Classification Search
CPC ....... A61B 8/461; A61B 8/485; A61B 8/5223; A61B 8/54; G01S 7/52022
See application file for complete search history.

(56) References Cited

U.S. PATENT DOCUMENTS

| | | | | |
|---|---|---|---|---|
| 2005/0015009 A1* | 1/2005 | Mourad | .............. | A61B 5/7267 600/438 |
| 2006/0036174 A1* | 2/2006 | Guracar | ................. | A61B 8/481 600/458 |
| 2007/0038083 A1* | 2/2007 | Srinivasan | ............ | G01S 15/584 600/437 |

(Continued)

FOREIGN PATENT DOCUMENTS

| | | | | |
|---|---|---|---|---|
| JP | 2014113323 A | 6/2014 | | |
| JP | 6053860 B2 | * 12/2016 | ............. | A61B 8/485 |

*Primary Examiner* — Yi-Shan Yang
*Assistant Examiner* — Alexei Bykhovski
(74) *Attorney, Agent, or Firm* — Lucas & Mercanti, LLP

(57) ABSTRACT

An ultrasound diagnostic device detecting shear wave propagation velocity through push pulse transmission. The ultrasound diagnostic device includes: a push pulse transmitter that transmits a push pulse; a detection wave transmitter/receiver that, following the push pulse transmission, transmits plane wave transmission detection waves towards a region of interest (ROI) inside a subject and receives reflection detection waves from the subject, to generate receive signals sequentially; a displacement detector that detects subject tissue displacement occurring inside the ROI due to a shear wave; and a shear wave analyzer that detects a shear wave propagation velocity based on the subject tissue displacement. The transmission detection waves at least include transmission detection waves transmitted by the detection wave transmitter/receiver at a first transmission interval and transmission detection waves transmitted by the detection wave transmitter/receiver at a second transmission interval longer than the first transmission interval.

11 Claims, 14 Drawing Sheets

(56) References Cited

U.S. PATENT DOCUMENTS

| | | | | |
|---|---|---|---|---|
| 2008/0139935 A1* | 6/2008 | Lin | ............... | A61B 8/485 |
| | | | | 600/443 |
| 2010/0286516 A1* | 11/2010 | Fan | ............... | A61B 8/08 |
| | | | | 600/438 |
| 2012/0136250 A1* | 5/2012 | Tabaru | ............... | A61B 8/08 |
| | | | | 600/438 |
| 2013/0211253 A1* | 8/2013 | Hsu | ............... | G01S 15/8915 |
| | | | | 600/438 |
| 2014/0018679 A1* | 1/2014 | Chen | ............... | A61B 8/085 |
| | | | | 600/438 |
| 2015/0094580 A1* | 4/2015 | Waki | ............... | A61B 8/5253 |
| | | | | 600/438 |
| 2016/0183926 A1* | 6/2016 | Asami | ............... | A61B 8/485 |
| | | | | 600/438 |
| 2016/0213352 A1* | 7/2016 | Toji | ............... | A61B 8/485 |
| 2017/0071577 A1* | 3/2017 | Seo | ............... | G01S 7/52071 |

\* cited by examiner

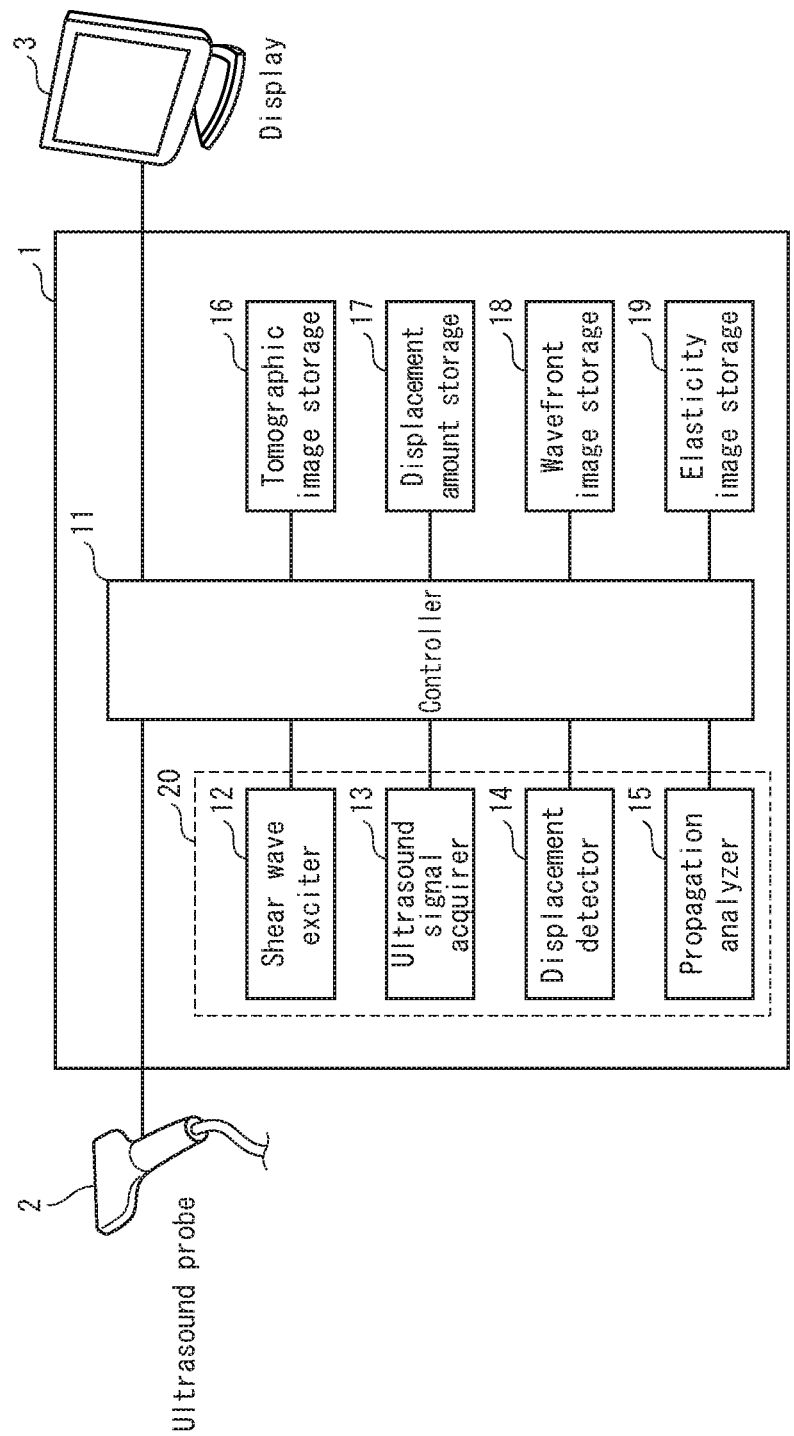

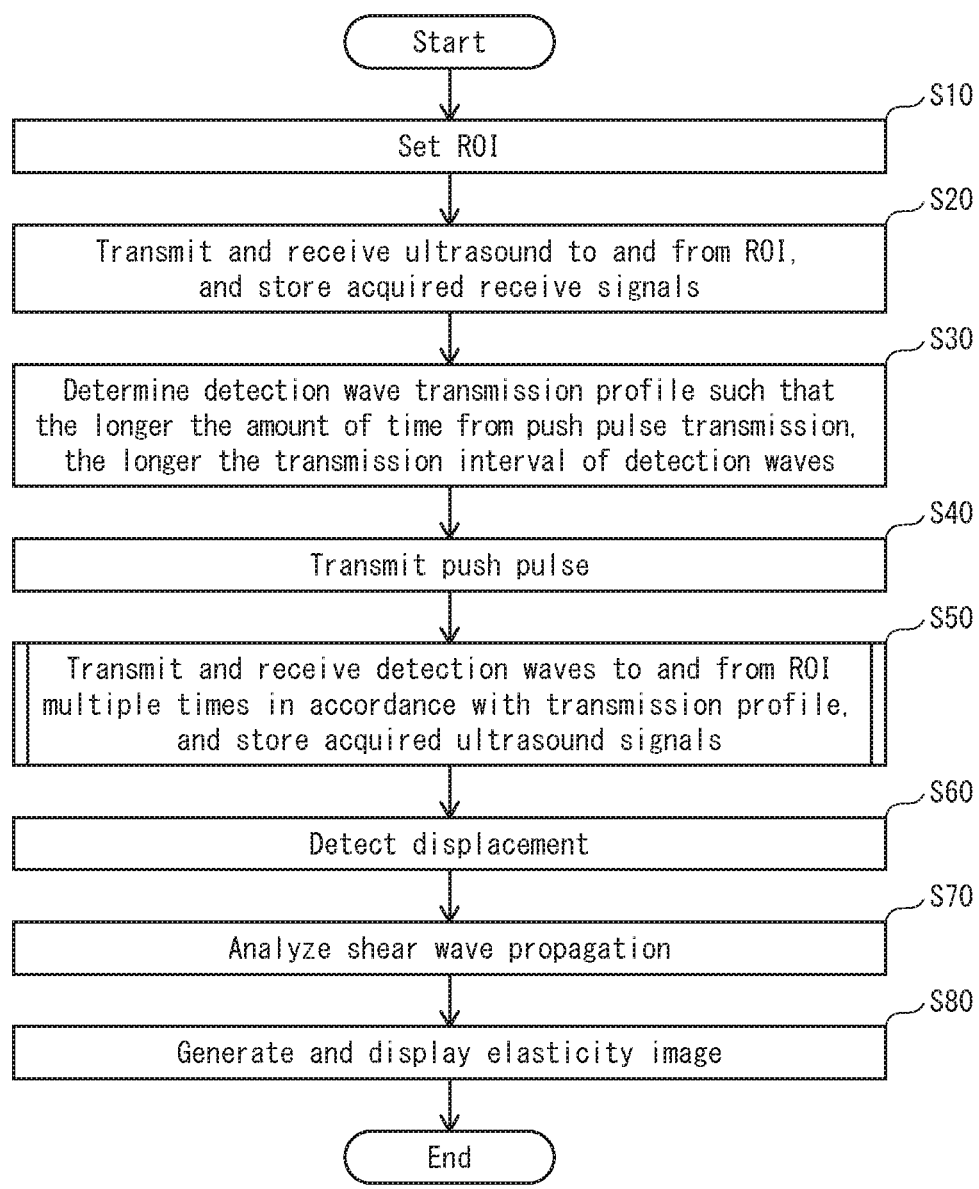

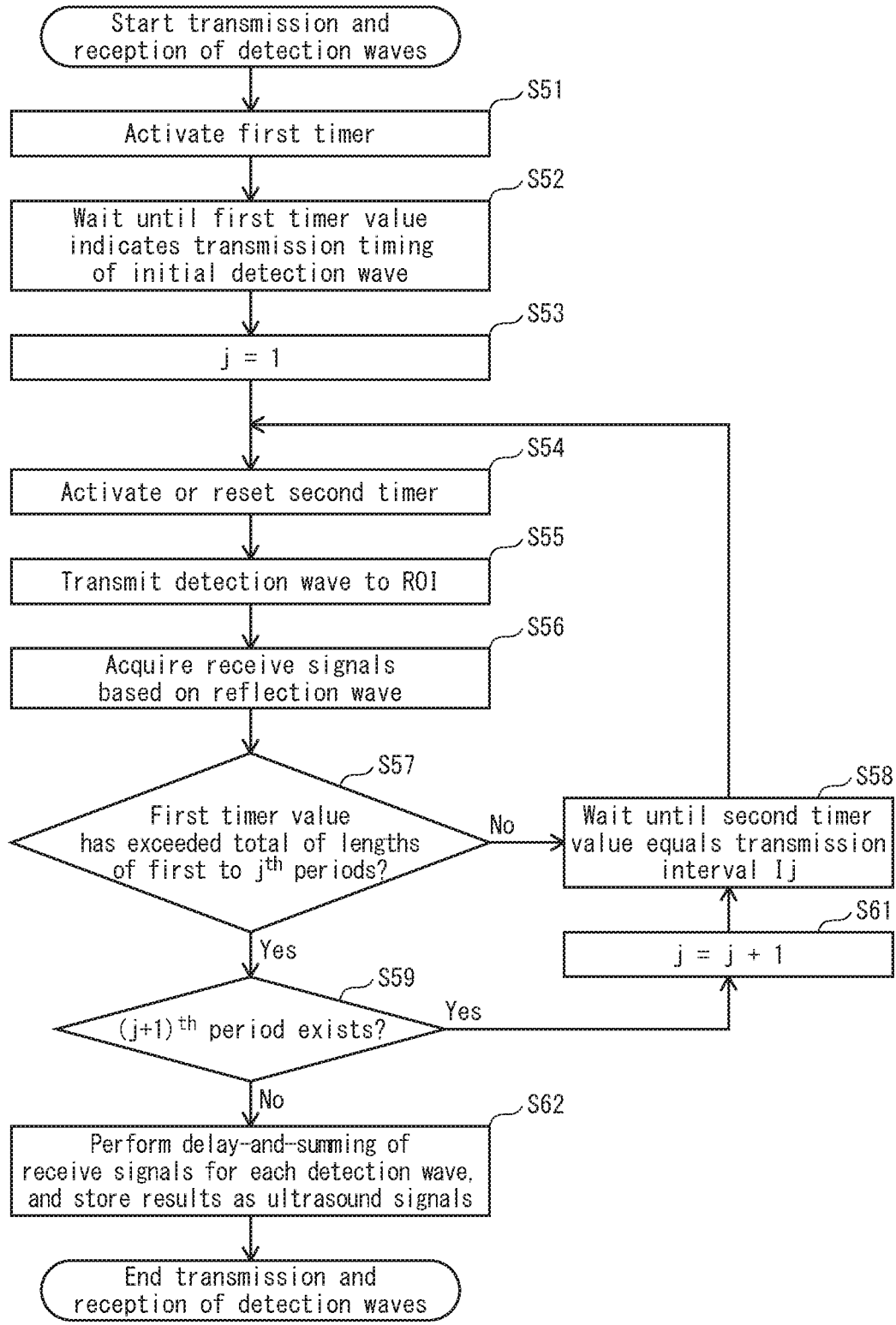

ULTRASOUND DIAGNOSTIC DEVICE AND ULTRASOUND SIGNAL PROCESSING METHOD

This application is based and claims the priority of Japanese Patent Application No. 2016-112802 filed on Jun. 6, 2016 in Japan, the contents of which is hereby incorporated by reference.

BACKGROUND OF THE INVENTION

(1) Field of the Invention

The present invention relates to imaging processing in ultrasound diagnostic devices. In particular, the present invention relates to measurement of tissue stiffness using shear waves.

(2) Description of the Related Art

In recent years, ultrasound diagnostic devices having a function of evaluating stiffness of subject tissues have become popular. In particular, one popular method that is used for evaluating stiffness of a subject tissue is generating a shear wave in a region of interest (ROI) in a subject, and measuring propagation velocity of the shear wave by acquiring tissue displacement in the ROI over time. This method has become popular for being capable of evaluating absolute stiffness (for example, an elastic modulus) of a tissue, as propagation velocity of a shear wave differs in accordance with the elastic modulus of the tissue. Further, one method that is used in generating shear waves is acoustic radiation force impulse (ARFI). When using ARFI, an ultrasound push pulse is transmitted to focus at a predetermined focal point, whereby the acoustic pressure of the push pulse generates displacement of subject tissue at the focal point.

SUMMARY OF THE INVENTION

Problems to be Solved by the Invention

For the measurement of shear wave propagation velocity, it is typically necessary to perform transmission and reception of detection waves (tracking pulses) at high speed following the transmission of the push pulse, to measure the chronological change in tissue displacement over the ROI. However, as disclosed in Japanese Patent Application Publication No. 2014-113323, frequent transmission/reception of ultrasound is likely to bring about heating of an ultrasound probe. Further, frequent ultrasound transmission/reception results in a large number of receive signals being acquired through the reception of detection waves, and thus increases processing amount in the detection of displacement.

Meanwhile, the more frequently detection waves are transmitted (i.e., the higher the frame rate), the higher the accuracy of the measurement of shear wave propagation velocity. Further, the spatially greater the ROI, the longer the amount of time required to measure the propagation of shear waves over the ROI. Due to this, measures such as simply reducing the frequency at which the transmission/reception of detection waves is performed or reducing the number of times the transmission/reception of detection waves is performed may result in low accuracy of the measurement of shear wave propagation velocity.

In view of the disclosure in Japanese Patent Application Publication No. 2014-113323, the present invention aims to reduce the frequency at which plane wave detection waves are sequentially transmitted/received following the transmission of a push pulse, while suppressing a decrease in accuracy of the measurement of shear wave propagation velocity.

Means for Solving the Problems

One aspect of the present invention is an ultrasound diagnostic device that uses an ultrasound probe to detect a propagation velocity of a shear wave generated at a specific part inside a subject by physically pushing tissue at the specific part by transmitting an ultrasound push pulse focusing on the specific part and then repeatedly transmitting and receiving ultrasound detection waves to and from inside the subject, the ultrasound diagnostic device including: ultrasound signal processing circuitry, the ultrasound signal processing circuitry including: a push pulse transmitter that transmits a push pulse towards the subject; a detection wave transmitter/receiver that, following the transmission of the push pulse, transmits plane wave transmission detection waves towards a region of interest (ROI) inside the subject and receives reflection detection waves corresponding to the transmission detection waves from the subject, to generate receive signals sequentially; a displacement detector that detects, from the receive signals, subject tissue displacement occurring inside the ROI at time points of reception of the reflection detection waves due to a shear wave generated by the push pulse; and a shear wave analyzer that detects a shear wave propagation velocity inside the ROI based on the subject tissue displacement, wherein the transmission detection waves at least include transmission detection waves transmitted by the detection wave transmitter/receiver at a first transmission interval and transmission detection waves transmitted by the detection wave transmitter/receiver at a second transmission interval longer than the first transmission interval.

Advantageous Effect of the Invention

The ultrasound diagnostic device pertaining to one aspect of the present invention optimizes an interval at which detection waves are transmitted to reduce the frequency at which detection waves are transmitted/received, while suppressing a decrease in accuracy of the measurement of shear wave propagation velocity.

BRIEF DESCRIPTION OF THE DRAWINGS

These and the other objects, advantages and features of the present invention will become apparent from the following description thereof taken in conjunction with the accompanying drawings, which illustrate specific embodiments of the present invention.

FIG. 1 is a block diagram illustrating an ultrasound diagnostic device 1 pertaining to embodiment 1.

FIG. 2 is a flowchart illustrating operations of the ultrasound diagnostic device 1 pertaining to embodiment 1.

FIG. 3 is a flowchart illustrating operations related to transmission and reception of detection waves, pertaining to embodiments of the present invention.

FIGS. 12A1 through 12A4, FIG. 12B, and FIG. 12C are schematics illustrating operations related to combining of shear wave propagation analysis results pertaining to embodiment 3.

DESCRIPTION OF EMBODIMENTS

Figure 4A:
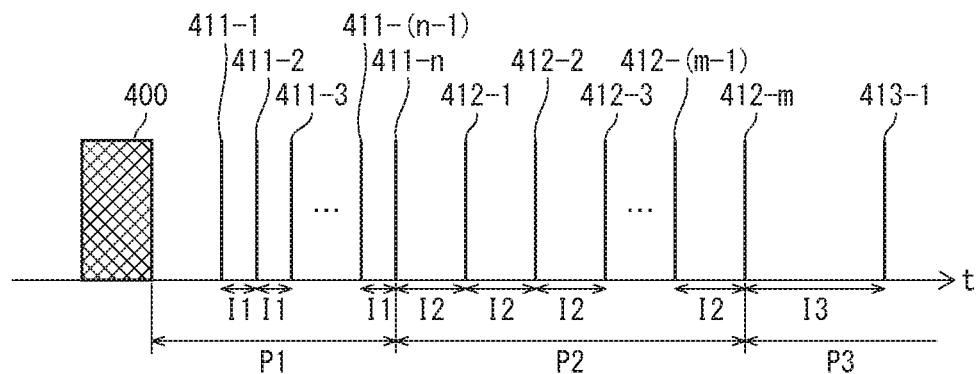
FIG. 4A is a schematic illustrating one example of a transmission profile of detection waves.

How Embodiments of Invention Were Arrived At

The inventor conducted various observations as to how the frequency of transmission/reception of plane wave detection waves can be reduced while suppressing a decrease in measurement accuracy, in an ultrasound diagnostic device that measures tissue stiffness with shear waves. Note that in the present disclosure, consideration is made of a case where plane wave detection waves are used as detection waves. This is because with plane wave detection waves, ultrasound transmission/reception can be performed with respect to an entirety of a ROI by performing transmission once, and thus, there is no need of transmitting detection waves at a frequency higher than the frame rate of B-mode images for detecting displacement.

As already discussed above, frequent transmission/reception of detection waves brings about heating of an ultrasound probe. Specifically, such heating is likely to occur when detection waves are transmitted/received frequently over a long period of time. Further, plane wave detection waves require a greater number of transducers for ultrasound transmission than focused detection waves, and thus, plane wave detection waves cause more heat to be generated than focused detection waves. As a result, ultrasound probe temperature may reach its upper limit in a short amount of time due to heating, which makes continuous operation of an ultrasound diagnostic device difficult. In order to overcome this problem, it is necessary to reduce ultrasound probe heat generation amount and/or to shorten the amount of time over which ultrasound probe heating occurs and reduce the frequency at which ultrasound probe heating occurs. In view of this, it is preferable to reduce the frequency of transmission/reception of detection waves and/or to shorten the amount of time over which frequent transmission/reception of detection waves is performed. Further, when transmission/reception is performed for a great number of times, a large number of receive signals are acquired and thus processing amount increases. Such increase in processing amount results in a long amount of time being required for an ultrasound diagnostic device to present results to a user (an examiner), and thus brings about latency in presentation of results and decrease in usability.

Meanwhile, simply reducing the frequency at which detection waves are transmitted/received leads to a decrease in temporal resolution in shear wave propagation analysis. This results in shear wave velocity being evened out in both the time and space domains, and thus, measurement accuracy decreases. That is, for example, it becomes difficult to detect stiff objects with small size, and interfaces between stiff tissues and surrounding tissues become unclear. Further, simply reducing the amount of time over which detection waves are transmitted/received results in only ROIs with small size being settable. This is because shear wave velocity is dependent upon tissue stiffness, and a reduction in measurement time naturally results in a reduction in spatial range of shear wave propagation that can be measured.

In view of such technical problems, the inventor arrived at ultrasound diagnostic devices pertaining to embodiments of the present invention, in connection with a technique of reducing frequency of transmission/reception of detection waves without affecting the accuracy of measurement of shear wave propagation velocity and ROI size.

The following describes ultrasound diagnostic devices pertaining to embodiments of the present invention in detail, with reference to the accompanying drawings.

Embodiment 1

FIG. 1 is a block diagram illustrating an ultrasound diagnostic device 1 pertaining to embodiment 1. The ultrasound diagnostic device 1 includes: a controller 11; a shear wave exciter 12; an ultrasound signal acquirer 13; a displacement detector 14; a propagation analyzer 15; a tomographic image storage 16; a displacement amount storage 17; a wavefront image storage 18; and an elasticity image storage 19. Further, the ultrasound diagnostic device 1 is configured so that an ultrasound probe 2 and a display 3 can be connected to the controller 11. FIG. 1 shows the ultrasound diagnostic device 1 with the ultrasound probe 2 and the display 3 connected thereto.

Among the constituent elements of the ultrasound diagnostic device 1, the shear wave exciter 12, the ultrasound signal acquirer 13, the displacement detector 14, and the propagation analyzer 15 constitute ultrasound signal processing circuitry 20.

The ultrasound probe 2, for example, has transducers (undepicted) arrayed along a one-dimensional direction. Each transducer, for example, is made of lead zirconate titanate (PZT). The ultrasound probe 2 receives electric signals from the controller 11 and converts the electric signals into ultrasound. The electric signals that the ultrasound probe 2 receives from the controller 11 may be electric signals (ARFI drive signals) generated by the shear wave exciter 12, or electric signals (detection drive signals) generated by the ultrasound signal acquirer 13. The ultrasound probe 2, with its transducer-side outer surface put in contact with a surface such as a subject skin surface, transmits an ultrasound beam composed of ultrasound waves emitted from its transducers towards a measurement target inside the subject. The ultrasound waves are generated by the transducers converting the ARFI drive signals or the detection drive signals into ultrasound. Further, the ultrasound probe 2 receives reflection detection waves from the measurement target. The reflection detection waves correspond to transmission detection waves that are based on detection drive signals. The ultrasound probe 2 converts each of these reflection detection waves into electric signals (transducer receive signals) by using its transducers, and supplies these transducer receive signals to the ultrasound signal acquirer 13 via the controller 11. Note that although the shear wave exciter 12 and the ultrasound signal acquirer 13 are described as separate elements, the ultrasound signal acquirer 13 may generate the ARFI drive signals by using the same configuration as it uses for generating the detection drive signals.

The shear wave exciter 12 generates the ARFI drive signals, which are electric signals causing the ultrasound probe 2 to transmit a push pulse. A push pulse is pulsed ultrasound for causing displacement of subject tissue, and is used to generate a shear wave in the subject. Specifically, the push pulse is ultrasound focusing at a given focal point in a ROI set inside the subject, and is composed of a greater number of waves than the transmission detection wave that is described in detail later in the present disclosure. Accordingly, the ARFI drive signals are pulsed electric signals with a different timing for each transducer, generated so that ultrasound waves transmitted from the transducers of the ultrasound probe 2 arrive at the focal point.

The ultrasound signal acquirer 13 generates the detection drive signals, which are electric signals causing the ultrasound probe 2 to transmit a transmission detection wave. Specifically, the detection drive signals are electric signals generated so that the transmission detection wave, transmitted from the transducers of the ultrasound probe 2, has a planar wavefront perpendicular to the direction in which the transmission detection wave travels. More specifically, the detection drive signals are generated so that all transducers have the same drive timing, or so that operation timing changes gradually from one end of the transducer array to the other at a fixed pitch. Thus, the transmission detection wave covers the entire ROI. Further, the ultrasound signal acquirer 13 generates acoustic line signals for the entire ROI by performing delay-and-summing of transducer receive signals that are acquired based on a reflection detection wave. The ultrasound signal acquirer 13 further outputs the acoustic line signals it has generated to the tomographic image storage 16 via the controller 11. Note that the ultrasound signal acquirer 13, by outputting detection drive signals to the controller 11 based on a predetermined profile, causes transmission detection waves to be transmitted repeatedly at predetermined timings. This is described in detail later in the present disclosure.

The displacement detector 14 acquires, from the tomographic image storage 16 via the controller 11, a group of acoustic image signals for a tomographic image (a tomographic image signal) to be used for detection of displacement and a group of acoustic line signals for a tomographic image to be used as a reference (a reference tomographic image signal). The reference tomographic image signal is used to detect displacement caused by a shear wave from the tomographic image signal, and is specifically a tomographic image signal captured from the ROI prior to the transmission of a push pulse. Further, the displacement detector 14 detects displacement at pixels of the tomographic image signal based on differences between the tomographic image signal and the reference tomographic image signal, and generates a displacement image by associating pixel coordinates with the displacement detected. The displacement detector 14 outputs the displacement image it has generated to the displacement amount storage 17 via the controller 11.

The propagation analyzer 15 acquires displacement images from the displacement amount storage 17 via the controller 11. The propagation analyzer 15 detects, from each displacement image, shear wave wavefront position, shear wave travel direction, and shear wave velocity at the time point at which the displacement image was acquired, and thereby generates a wavefront image. Further, the propagation analyzer 15 generates an elasticity image by calculating an elastic modulus for subject tissues corresponding to the pixels in the displacement image, based on the shear wave wavefront position, the shear wave travel direction, and the shear wave velocity. The propagation analyzer 15 outputs the wavefront image it has generated to the wavefront image storage 18 via the controller 11, and outputs the elasticity image it has generated to the elasticity image storage 19 via the controller 11.

The controller 11, in addition to controlling the constituent elements described above, outputs the elasticity image generated by the propagation analyzer 15 to the display 3.

The tomographic image storage 16, the displacement amount storage 17, the wavefront image storage 18, and the elasticity image storage 19 respectively store tomographic image data, displacement image data, wavefront image data, and elasticity image data. The tomographic image storage 16, the displacement amount storage 17, the wavefront image storage 18, and the elasticity image storage 19 are each implemented, for example, by using a random access memory (RAM), a flash memory, a hard disk, or an optical disc. Note that two or more among the tomographic image storage 16, the displacement amount storage 17, the wavefront image storage 18, and the elasticity image storage 19 may be implemented by using a single storage medium. Further, one or more among the tomographic image storage 16, the displacement amount storage 17, the wavefront image storage 18, and the elasticity image storage 19 may be configured to be external to the ultrasound diagnostic device 1, connected to the ultrasound diagnostic device 1 via an interface such as a universal serial bus (USB) or an external Serial AT Attachment (eSATA), or may be implemented as a resource such as a file server or a network attached storage (NAS) that the ultrasound diagnostic device 1 is capable of accessing via a network.

The controller 11, the shear wave exciter 12, the ultrasound signal acquirer 13, the displacement detector 14, and the propagation analyzer 15 may each be implemented by using hardware such as a field programmable gate array (FPGA) or an application specific integrated circuit (ASIC). Note that some or all of these constituent elements may be implemented on a single FPGA or a single ASIC. Further, each of these constituent elements may be individually implemented by using a combination of a memory, software, and a programmable device such as a central processing unit (CPU) or a graphic processing unit (GPU). Alternatively, two or more of these constituent elements may be implemented in integrated manner by using a combination of memory, software, and a programmable device such as a CPU or a GPU.

Operations

The following describes operations of the ultrasound diagnostic device 1 pertaining to embodiment 1. FIG. 2 is a flowchart illustrating operations of the entire ultrasound diagnostic device 1.

First, the controller 11 sets a ROI (Step S10). For example, the controller 11 sets the ROI by displaying the newest tomographic image stored in the tomographic image storage 18 on the display 3, and having the examiner specify a ROI by using an input device (undepicted) such as a touch panel, a mouse, and/or a track ball. Note that the controller 11 need not set a ROI in such a manner, and instead, may for example set an entirety of a tomographic image as a ROI or set a certain region of a tomographic image, at least including a central portion of the tomographic image, as a ROI. Further, the controller 11 may newly acquire a tomographic image upon setting a ROI.

Subsequently, transmission and reception of ultrasound to and from the subject is performed, and receive signals acquired are stored (Step S20). Specifically, the following operations are performed. First, a transmission event is performed as follows. First, the ultrasound signal acquirer 13 generates a pulsed transmission signal. Subsequently, the ultrasound signal acquirer 13 generates detection drive signals for the transducers of the ultrasound probe 2, by performing transmission beam forming of setting a delay time to be applied to the transmission signal, for each transducer of the ultrasound probe 2. When the transducers of the ultrasound probe 2 convert the corresponding detection drive signals into ultrasound, an ultrasound beam is transmitted towards the inside of the subject. Subsequently, the transducers of the ultrasound probe 2 acquire ultrasound reflection from the inside of the subject, and convert the reflection ultrasound waves into transducer receive signals. Then, the ultrasound signal acquirer 13 generates acoustic line signals by performing delay-and-summing of the transducer receive signals. The controller 11 acquires, from the ultrasound signal acquirer 13, a group of acoustic line signals that have been generated through one transmission event and that compose one tomographic image, and stores the group of acoustic line signals as a reference tomographic image signal to the tomographic image storage 16.

Following this, a detection wave transmission profile is determined (Step S30). The transmission profile is determined so that the longer the amount of time from completion of transmission of a push pulse, the longer the interval between transmissions of detection waves. In this embodiment, a predetermined transmission profile such as that illustrated in FIG. 4A is used. FIG. 4A is a timing chart illustrating the detection wave transmission profile pertaining to embodiment 1. Here, for a first period P1, which is a period following the transmission of a push pulse 400, the detection wave transmission interval is set to I1. Thus, a second detection wave 411-2 is transmitted after interval I1 elapses from the transmission of a first detection wave 411-1. Transmission of detection waves at the interval I1 is performed until an $n^{th}$ detection wave 411-n is finally transmitted. For a second period P2 following the first period P1, the detection wave transmission interval is set to I2, which is longer than I1. Thus, a detection wave 412-1 is transmitted after interval I2 elapses from the transmission of the detection wave 411-n. Further, a detection wave 412-2 is transmitted after interval I2 elapses from the transmission of the detection wave 412-1. Transmission of detection waves at the interval I2 is performed until an $m^{th}$ detection wave 412-m is finally transmitted. For a third period P3 following the second period P2, the detection wave transmission interval is set to I3, which is longer than I2. Thus, a detection wave 413-1 is transmitted after interval I3 elapses from the transmission of the detection wave 412-m. As such, the transmission profile is such that the transmission interval increases in levels as the amount of time between the time point of transmission of the push pulse 400 and the time point of detection wave transmission increases. For example, the first period P1 is 3.8 ms, and the transmission interval I1 is 100 μs (which means that transmission is performed 38 times). The second period P2 is 3.8 ms, and the transmission interval I2 is 200 μs (which means that transmission is performed 19 times). The third period P3 is 11.2 ms, and the transmission interval I3 is 400 μs (which means that transmission is performed 28 times). Further, a fourth period P4 is 12 ms, and a transmission interval I4 is 800 μs (which means that transmission is performed 15 times). Thus, transmission is performed one hundred times within a period of 30.8 ms.

Subsequently, a push pulse is transmitted (Step S40). Specifically, the shear wave exciter 12 generates a pulsed ARFI signal. Subsequently, the shear wave exciter 12 generates ARFI drive signals for the transducers of the ultrasound probe 2, by performing transmission beam forming of setting a delay time to be applied to the ARFI signal, for each transducer of the ultrasound probe 2. When the transducers of the ultrasound probe 2 convert the corresponding ARFI drive signals into ultrasound, a push pulse is transmitted towards the inside of the subject.

Figure 5A:
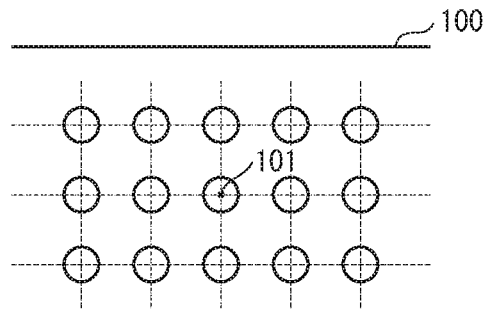
FIGS. 5A through 5E are schematics illustrating shear wave generation and propagation.
Figure 5B:
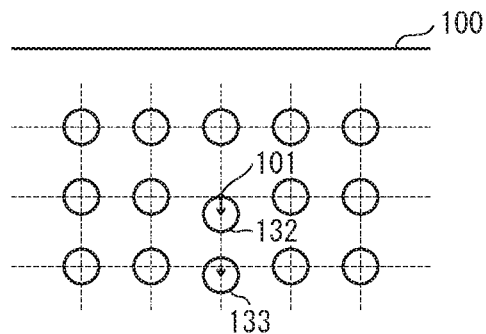
Figure 5C:
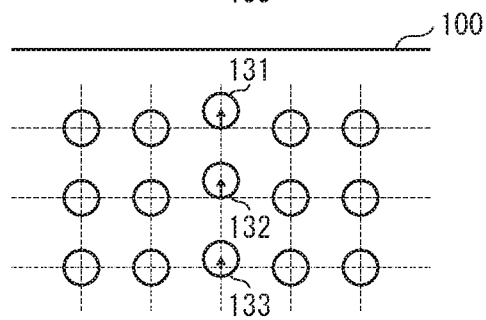
Figure 5D:
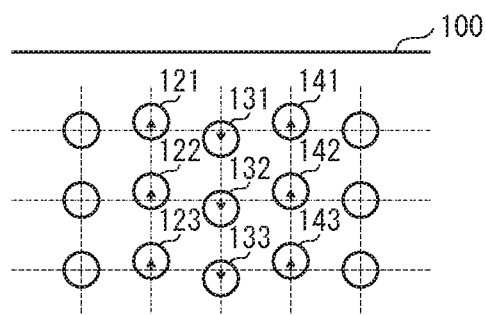
Figure 5E:
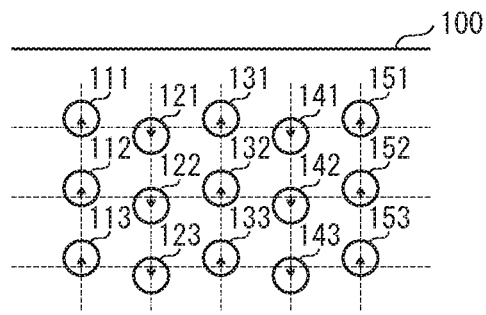

The following describes how a push pulse generates a shear wave, with reference to FIGS. 5A through 5E. FIG. 5A illustrates tissues at a subject region corresponding to a ROI, before the application of a push pulse. Note that in FIGS. 5A through 5E, the circles indicate some subject tissues at the ROI, and the intersections of the dashed lines indicate centers of the tissues when not under load. When a push pulse is applied to a focal point 101 with the ultrasound probe 2 put in close contact with a skin surface 100, a tissue 132 at the focal point 101 is pushed and moves in the travel direction of the push pulse, as illustrated in FIG. 5B. Further, a tissue 133 that is located in the travel direction of the push pulse from the tissue 132 is pushed by the tissue 132 and moves in the push pulse travel direction. When the transmission of the push pulse is completed, the tissues 132, 133 attempt to return to their original positions, and therefore a tissue 131, the tissue 132, and the tissue 133 start vibrating along the push pulse travel direction, as illustrated in FIG. 5C. Then, the vibration propagates to tissues 121, 122, 123 and tissues 141, 142, 143, which are adjacent to the tissues 131, 132, 133, as illustrated in FIG. 5D. Further, the vibration further propagates to tissues 111, 112, 113 and tissues 151, 152, 153, as illustrated in FIG. 5E. Accordingly, in the subject, vibration propagates in a direction perpendicular to the direction of vibration. As such, a shear waves is generated where the push pulse is applied, and the shear wave propagates inside the subject.

The following provides description referring to FIG. 2 once again. Subsequently, detection wave transmission/reception with respect to the ROI is performed multiple times, and ultrasound signals that are acquired are stored (Step S50). The following provides detail description with reference to FIG. 3. FIG. 3 is a flowchart illustrating the details of Step S50. First, the ultrasound signal acquirer 13 activates a first timer (Step S51), and waits until the value of the first timer indicates the transmission timing of an initial detection wave (Step S52). Subsequently, the ultrasound signal acquirer 13 initializes a period counter j (i.e., sets one to the period counter j) (Step S53), and then activates a second timer (Step S54) and transmits a detection wave to the ROI (Step S55). Note that the processing by the ultrasound signal acquirer 13 in Step S55 is similar to that in Step S20. That is, the ultrasound signal acquirer 13 generates a pulsed transmission signal, and generates detection drive signals for the transducers of the ultrasound probe 2 by performing transmission beam forming of setting a delay time to be applied to the transmission signal, for each transducer of the ultrasound probe 2. When the transducers of the ultrasound probe 2 convert the corresponding detection drive signals into ultrasound, a transmission detection wave is transmitted towards the inside of the subject. Subsequently, the transducers of the ultrasound probe 2 acquire a reflection detection wave from the inside of the subject, and convert the reflection detection wave into transducer receive signals. The ultrasound signal acquirer 13 acquires and stores these transducer receive signals (Step S56). Then, the ultrasound signal acquirer 13 judges whether the value of the first timer has exceeded the total of the lengths of the first to $j^{th}$ periods (the length of the first period P1 in this case) (Step S57). The result of Step S57 is No when Step S57 is initially performed after the transmission of the initial detection wave. In this case, the ultrasound signal acquirer 13 waits until the value of the second timer equals a transmission interval Ij (i.e., transmission interval I1 in this case) (Step S58), and then resets the second timer to zero (Step S54) and transmits a detection wave to the ROI (Step S55). Accordingly, the loop from Step S54 to Step S58 causes detection waves to be repeatedly transmitted at the transmission interval I1. When the first period P1 ends and the final detection wave has been transmitted, the result of Step S57 becomes Yes. Then, if a second period P2 exists (Yes in Step S59), the ultrasound signal acquirer 13 increments j to two (Step S61). Following this, after waiting until the value of the second timer equals the transmission interval Ij (i.e., transmission interval I2 in this case) (Step S58), the ultrasound signal acquirer 13 resets the second timer to zero (Step S54) and transmits a detection wave to the ROI (Step S55). Accordingly, the initial detection wave for the second period P2 is transmitted after the transmission interval I2 elapses from the transmission of the final detection wave for the first period P1. Following this, processing similar to that during the first period P1 is performed, and thus, detection waves are repeatedly transmitted at the transmission interval I2 during the second period P2. When the second period P2 ends and the final detection wave has been transmitted, the result of Step S57 becomes Yes. Then, if a third period P3 exists (Yes in Step S59), the ultrasound signal acquirer 13 increments j to three (Step S61). Following this, after waiting until the value of the second timer equals the transmission interval Ij (i.e., transmission interval I3 in this case) (Step S58), the ultrasound signal acquirer 13 resets the second timer to zero (Step S54) and transmits a detection wave to the ROI (Step S55). By such processing being repeated, detection waves are transmitted in accordance with the transmission profile up to the final $j^{th}$ period. Finally, for each detection wave, the ultrasound signal acquirer 13 performs delay-and-summing of transducer receive signals and generates acoustic line signals (Step S62). For each detection wave, the controller 11 acquires acoustic line signals generated for the detection wave from the ultrasound signal acquirer 13, and stores the acoustic line signals in the tomographic image storage 16 as a tomographic image signal.

Subsequently, the displacement detector 14 detects pixel displacement (Step S60). Specifically, the displacement detector 14 first acquires the reference tomographic image signal having been stored to the tomographic image storage 16 in Step S20. Then, the displacement detector 14, for each tomographic image signal having been stored to the tomographic image storage 16 in Step S50, detects pixel displacement at the time point when the reflection detection wave corresponding to the tomographic image signal was received based on differences between the reference tomographic image signal and the tomographic image signal. Specifically, the displacement detector 14 performs correlation of the tomographic image signal and the reference tomographic image signal to determine which pixel of the reference tomographic image signal a pixel of the tomographic image signal corresponds to, and specifies a difference in coordinate position as the displacement of the pixel of the tomographic image signal. Note that the detection of displacement need not be performed using correlation, and instead may be performed by using any available technique that enables detection of motion amounts between two tomographic image signals, such as pattern matching. For example, displacement of pixels of a tomographic image signal can be detected by dividing the tomographic image signal into regions with a predetermined size (e.g., 8×8 pixel areas), and by performing pattern matching between each of these regions and the reference tomographic image signal. The following describes an example of a pattern matching method. First, differences in luminance values of corresponding pixels are detected, for example between each region and a reference region of a same size in the reference tomographic image signal, and a sum of absolute values of the differences is calculated. The combination of region and reference region for which the sum is smallest is considered to be the same region and a distance between a reference point of the region (for example, a top left corner) and a reference point of the reference region is detected as a displacement amount. Note that a tomographic image need not be divided into 8'8 pixel regions. That is, the predetermined size need not be 8×8 pixels. Further, in place of a sum of absolute values of differences between luminance values, a sum of squares of differences between luminance values may be used, for example. Further, in the detection of displacement through correlation, pattern matching, or the like, the difference between y coordinates of corresponding pixels (i.e., the difference in depths of the corresponding pixels) may be used as a displacement amount, instead of using the difference between coordinate positions of corresponding pixels. This is because shear waves basically propagate in an element array direction (x-axis direction), and thus shear waves bring about displacement in a direction perpendicular to the direction in which they propagate, which is basically a depth direction (y-axis direction). Through such processing, amounts of movement of subjects tissue corresponding to pixels in tomographic image signals, brought about by a push pulse or a shear wave, are calculated as displacement amounts. The displacement detector 14 further generates a displacement image by associating, with coordinates of each pixel of a tomographic image signal, displacement detected at the pixel. Further, the displacement detector 14 outputs the displacement image it has generated to the displacement amount storage 17.

Subsequently, the propagation analyzer 15 analyzes shear wave propagation (Step S70). Specifically, the propagation analyzer 15 extracts shear wave wavefronts from each displacement image and generates a wavefront image from the shear wave wavefronts so extracted. From this wavefront image, positions of shear wave wavefronts, amplitudes of shear waves, travel directions of shear waves, and velocities of shear waves can be easily detected. The generation of a wavefront image is performed, for example, through extraction of displacement regions, thinning, spatial filtering, and temporal filtering performed in this order.

Figure 6A:
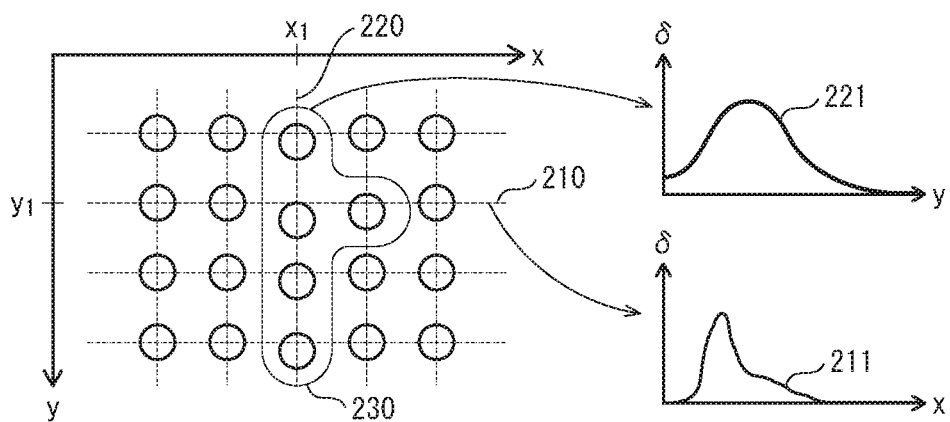
FIGS. 6A through 6E are schematics illustrating operations related to shear wave propagation analysis pertaining to embodiment 1.

The following describes the processing in specific, with reference to FIGS. 6A through 6E. FIG. 6A illustrates one example of a displacement image. Similar to FIGS. 5A through 5E, the circles in FIG. 6A indicate subject tissues at the ROI, and the intersections of the dashed lines in FIG. 6A indicate positions of the subject tissues before application of a push pulse. The propagation analyzer 15, for each y coordinate, indicates displacement amount δ as a function of coordinate x, and extracts an x-axis direction area with great displacement amount δ by using dynamic thresholding. Similarly, the propagation analyzer 15, for each x coordinate, indicates displacement amount δ as a function of coordinate y, and extracts a y-axis direction area with great displacement amount δ by using dynamic thresholding. Here, dynamic thresholding involves determining a threshold for a processing-target area by performing signal analysis or image analysis for an inside of the processing-target area. Thus, the threshold changes in accordance with amplitudes, maximum values, and/or the like of signals in the target area. FIG. 6A illustrates graphs 211 and 221. Graph 211 indicates displacement amounts along a straight line 210 corresponding to $y=y_1$. Graph 221 indicates displacement amounts along a straight line 220 corresponding to $x=x_1$. Accordingly, displacement area 230 over which the displacement amount δ is greater than a threshold can be extracted.

Figure 6B:
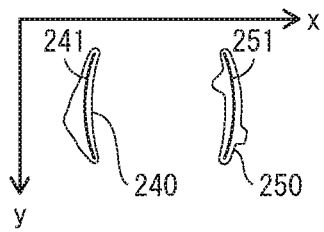
Figure 6C:
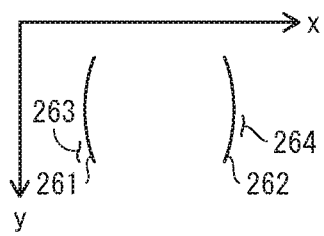
Figure 6D:
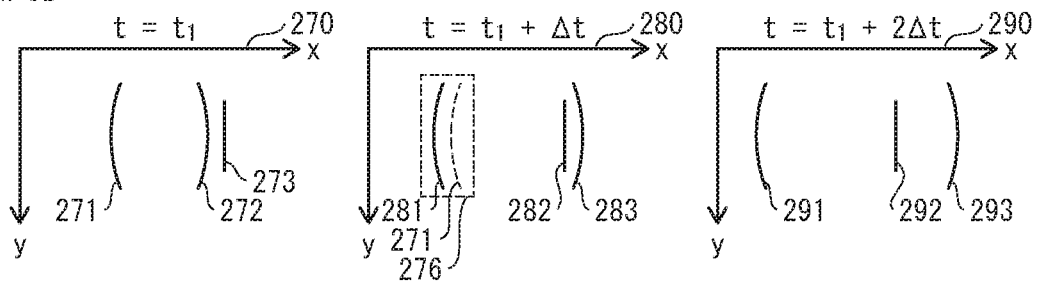
Figure 6E:
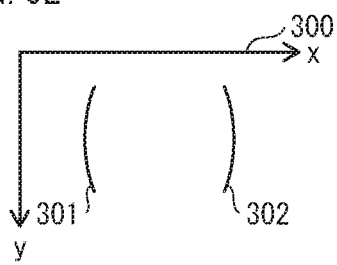

Subsequently, the propagation analyzer 15 extracts wavefronts by performing thinning on displacement areas. Displacement areas 240 and 250 illustrated in schematic FIG. 6B are each an area having been extracted as a displacement area. The propagation analyzer 15 extracts wavefronts by using, for example, the Hilditch thinning algorithm. For example, in schematic FIG. 6B, wavefronts 241 and 251 are respectively extracted from the displacement areas 240 and 250. Note that the algorithm used for thinning need not be the Hilditch thinning algorithm, and any thinning algorithm may be used. Alternatively, for each displacement area, processing of removing coordinate positions with displacement amounts δ no greater than a threshold may be performed repeatedly while gradually increasing the threshold, until the displacement area becomes a line having single pixel width.

Subsequently, the propagation analyzer 15 performs spatial filtering on wavefront image data with respect to which thinning has been performed, and thereby removes wavefronts with short lengths. For example, lengths of the wavefronts having been extracted are detected, and wavefronts having lengths shorter than half the average of lengths of all wavefronts are deleted as noise. Specifically, as illustrated in the wavefront image illustrated in FIG. 6C, the average of lengths of wavefronts 261 through 264 is calculated, and the wavefronts 263 and 264 having lengths shorter than half the average so calculated are deleted as noise. Thus, erroneously detected wavefronts can be deleted.

The propagation analyzer 15 performs the extraction of displacement areas, thinning, and spatial filtering for each displacement image. Accordingly, wavefront images corresponding one-to-one to displacement images are generated.

Finally, the propagation analyzer 15 performs temporal filtering on multiple wavefront images to remove non-propagating wavefronts. Specifically, the propagation analyzer 15, taking at least two temporally successive wavefront images, detects the temporal change of wavefront positions in these wavefront images, and removes wavefronts having abnormal velocity as noise. Here, for example, propagation analyzer 15 detects the temporal change in wavefront positions in three wavefront images, namely wavefront image 270 for time point $t=t_1$, wavefront image 280 for time point $t=t_1+\Delta t$, and wavefront image 290 for time point $t=t_1+2\Delta t$. For example, for wavefront 271 in the wavefront image 270, correlation is performed in area 276 in the wavefront image 280, which is an area of the wavefront image 280 centered on the same position as the wavefront 271 and within which shear waves can travel in the direction perpendicular to the wavefronts (i.e., x-axis direction in FIG. 6D within the time amount Δt. Here, correlation is performed in an area including both an x-axis positive direction side (right side in the drawing) of the wavefront 271 and an x-axis negative direction side (left side in the drawing) of the wavefront 271. This enables detection of both incident and reflected shear waves. Thus, it is detected that the wavefront 271 has travelled to the wavefront 281 in the wavefront image 280, and the distance by which the wavefront 271 has traveled over the time amount Δt is calculated. Similarly, for each of the wavefronts 272 and 273, correlation is performed in an area in the wavefront image 280 that is centered on the same position as the wavefront and within which shear waves can travel in the direction perpendicular to the wavefronts within the time amount Δt.

Consequently, it is detected that the wavefronts 272 and 272 have respectively traveled to the positions of the wavefronts 283 and 282. Similar processing is performed for the combination of the wavefront image 280 and the wavefront image 290, whereby it is detected that the wavefronts 281, 282, and 283 have respectively travelled to the positions of the wavefronts 291, 292, and 293. Here, the same wavefront that is shown as the wavefronts 273, 282, and 292 has travelled a significantly smaller distance (has propagated at a significantly lower velocity) than the rest of the wavefronts. Such a wavefront is deleted as noise because the possibility is high of such wavefront having been erroneously detected. Thus, wavefronts 301 and 302 are detected as illustrated in the wavefront image 300 shown in FIG. 6E.

Figure 7A:
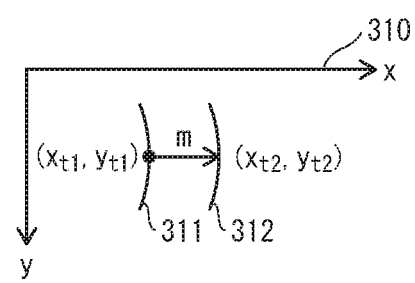
FIGS. 7A and 7B are schematics illustrating processing related to elastic modulus measurement pertaining to embodiment 1.

Further, the propagation analyzer 15 uses wavefront images for different time points and information indicating the correspondence between wavefronts to calculate positions and velocities of wavefronts. Here, the information indicating the correspondence between wavefronts indicates wavefronts in different wavefront images that correspond to the same wavefront. For example, in FIG. 6D, when it is detected that the wavefront 272 has travelled to the position of the wavefront 282, the information indicates that the wavefront 272 and the wavefront 283 correspond to the same wavefront. The following describes calculation of wavefront velocities, with reference to FIGS. 7A and 7B. FIG. 7A shows a single wavefront image 310 yielded by combining a wavefront image at time point $t_1$ and a wavefront image at time point $t_2$ ($t_1<t2$). Here, suppose that correspondence information exists indicating that the wavefront 311 at time point $t_1$ and the wavelength 312 at time point $t_2$ correspond to the same wavefront. Based on this correspondence information, a coordinate position $(x_{t2}, y_{t2})$ along the wavefront 312 is detected that corresponds to a coordinate position $(x_{t1}, y_{t1})$ along the wavefront 311. Based on this, it can be estimated that a shear wave passing through the coordinate position $(x_{t1}, y_{t1})$ at time point $t_1$ passes through the coordinate position $(x_{t2}, y_{t2})$ at time point $t_2$. Thus, it can be estimated that a velocity $v(x_{t1}, y_{t1})$ of the shear wave passing through the coordinate position $(x_{t1}, y_{t1})$ can be calculated by dividing a distance d between the coordinate positions $(x_{t1}, y_{t1})$ and $(x_{t2}, y_{t2})$ by required time amount $\Delta t=t_2-t_1$. That is, the velocity $v(x_{t1}, y_{t1})$ of the shear wave is expressible as: $v(x_{t1}, y_{t1})=d/\Delta t=\sqrt{\{(x_{t2}-x_{t1})^2+(y_{t2}-y_{t1})^2\}}/\Delta t$. The propagation analyzer 15 performs this processing for every wavefront, acquires shear wave velocity at every coordinate position that a wavefront passes through, and generates a velocity distribution diagram by associating pixels with shear wave velocities. Further, the propagation analyzer 15 holds this velocity distribution diagram.

The following provides description referring to FIG. 2 once again. Finally, an elasticity image is generated and displayed (Step S80). Specifically, the propagation analyzer 15 first calculates, for each pixel of the velocity distribution diagram, an elastic modulus based on shear wave velocity at the pixel, and generates an elasticity image by associating pixels with elastic moduli. An elastic modulus $E(x_t, y_t)$ for a coordinate position $(x_t, y_t)$ can be calculated as follows by using a shear wave velocity $v(x_t, y_t)$ at the coordinate position: $E(x_t, y_t)=2(1+\gamma)\rho \times v(x_t, y_t)^2$. Here, $\gamma$ denotes a Poisson's ratio of a tissue at the coordinate position $(x_t, y_t)$ and $\rho$ denotes density of the tissue. For simplification, the elastic modulus $E(x_t, y_t)$ can for example be calculated as follows assuming $\gamma=0.5$ and $\rho=1$ g/cm$^3$: $E(x_t, y_t) \approx 3 \times v(x_t, y_t)^2$.

Figure 7B:
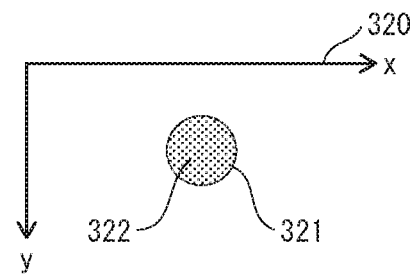

Pixels are associated with their elasticity moduli by, for example, mapping color information. Accordingly, for example as illustrated in FIG. 7B, a color-coded elasticity image 320 is generated. For example, in the elasticity image 320, coordinate positions with elasticity moduli no smaller than a predetermined value may be colored red, coordinate positions with elasticity moduli smaller than the predetermined value may be colored green, and coordinate points for which elasticity moduli could not be acquired may be colored black. Classification of elasticity moduli need not be performed through binary classification, and classification and color-coding may be performed with multiple predetermined levels. In FIG. 7B, an area 322 is an area of elasticity moduli no smaller than the predetermined value, and corresponds to an inclusion 321. Note that while the inclusion 321 is clearly illustrated in FIG. 7B for the sake of explanation, the inclusion 321 actually does not directly appear in an elasticity image. The propagation analyzer 15 outputs the elasticity image it has generated to the controller 11, and the controller 11 outputs the elasticity image to the elasticity image storage 19. The controller 11 causes the elasticity image and an ultrasound image to be displayed. Specifically, the controller 11 performs geometric conversion to convert each of the elasticity image generated in Step S80 and the reference tomographic image signal acquired in Step S20 into image data for screen display. The controller 11 outputs the geometrically-converted elasticity image and an ultrasound image yielded through the geometrical conversion to the display 3.

Effect of Detection Wave Transmission Profile on Shear Wave Propagation Analysis The following describes the effect that the detection wave transmission profile has on the shear wave propagation analysis.

Figure 4B:
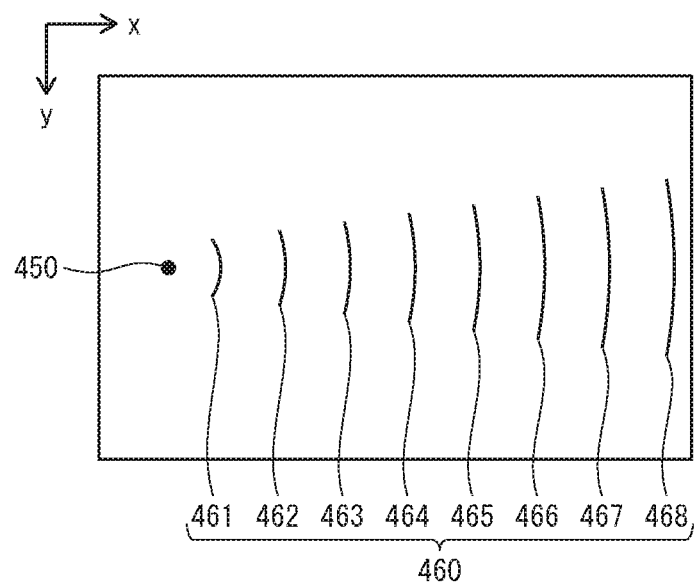
FIGS. 4B and 4C are schematics each illustrating a relationship between a transmission profile and shear wave wavefronts.

First, description is provided of a case when propagation velocity of a shear wave is high, with reference to FIG. 4B. FIG. 4B is a schematic illustrating an example where a shear wave leaves the ROI during the first period P1.

When propagation velocity of a shear wave is high, a shear wave generated at a push pulse focal point 450 reaches an outer boundary of the ROI and leaves the ROI during the first period P1. In this case, no wavefront is detected in the second period P2 and subsequent periods, and only wavefront group 460 corresponding to the first period P1 is detected in the ROI. That is, only wavefronts 461 through 468 are detected in the ROI. Thus, the transmission interval between any pair of two successive detection waves is always the shortest transmission interval I1. Due to this, the shear wave propagation analysis can be performed without decrease in temporal resolution at any location, and thus, a decrease in accuracy of measurement of shear wave velocity can be suppressed.

Figure 4C:
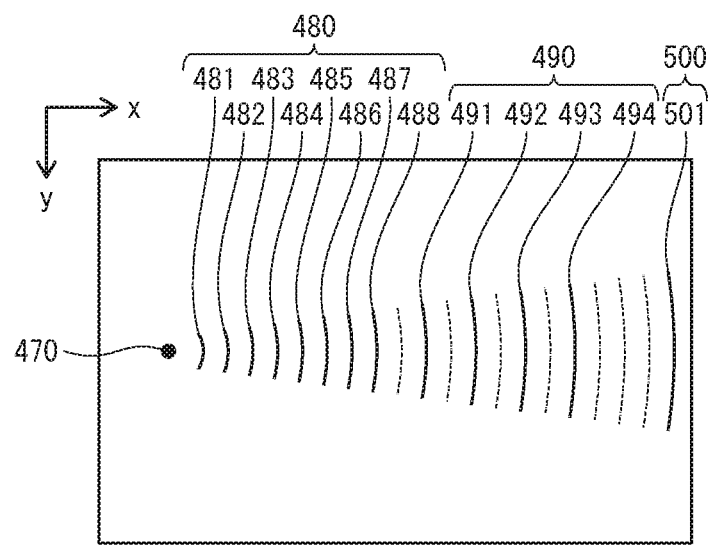

Further, description is provided of a case when propagation velocity of a shear wave is low, with reference to FIG. 4C. Specifically, FIG. 4C is a schematic illustrating an example where a shear wave leaves the ROI during the third period P3.

When propagation velocity of a shear wave is low, a shear wave generated at a push pulse focal point 470 is still propagating through the ROI even after the second period P2 ends. In this case, a wavefront group 480 corresponding to the first period P1 (i.e., wavefronts 481 through 488), a wavefront group 490 corresponding to the second period P2 (i.e., wavefronts 491 through 494), and a wavefront group 500 corresponding to the third period P3 (i.e., a wavefront 501) are detected. Here, because the propagation velocity of the shear wave is low, a decrease in temporal and spatial resolution brought about by the wavefront of the shear wave traveling too long a distance during the transmission interval I2 pertaining to the second period P2 does not occur, and thus the shear wave propagation analysis can be performed without any decrease in accuracy. That is, the accuracy of measurement of shear wave velocity does not decrease because detection waves are transmitted during the first period P1 and the second period P2 at intervals short enough for accurate shear wave propagation analysis. Meanwhile, for the wavefront 501 acquired during the third period P3, a decrease in spatial and temporal resolution is brought about due to the wavefront of the shear wave traveling a long distance during the transmission interval I3. However, the third period P3 is temporally far from the time point of push pulse transmission. Due to this, in the third period P3, shear wave energy has already decayed and the amount of displacement brought about by the shear wave has a small absolute value. As such, even if detection waves were transmitted at the transmission interval I1 during the third period P3, the result of the shear wave propagation analysis would still not have good accuracy. Accordingly, even if the transmission interval I3 during the third period P3 is longer than an interval required for accurate shear wave propagation analysis, the influence of the transmission interval I3 is not significant merely bringing about a further decrease in accuracy at an area where accuracy is low.

Figure 8A:
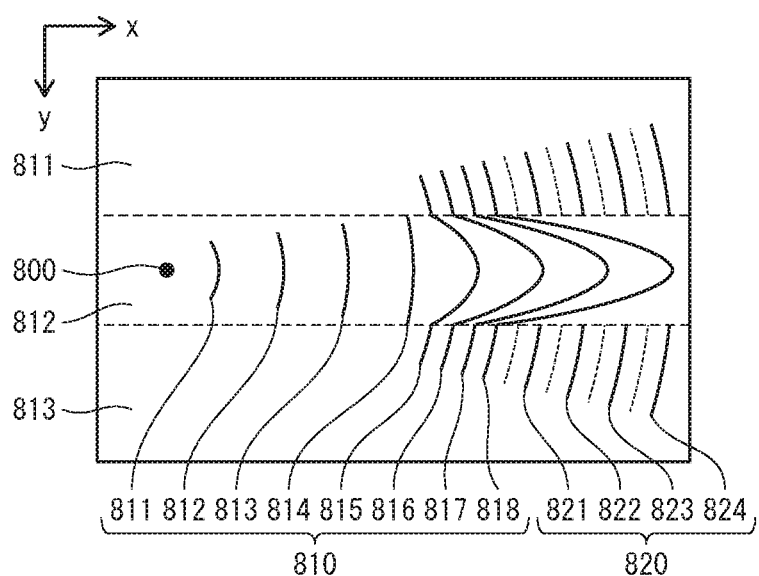
FIGS. 8A through 8C are schematics each illustrating a relationship between a transmission profile and shear wave wavefronts.
Figure 8B:
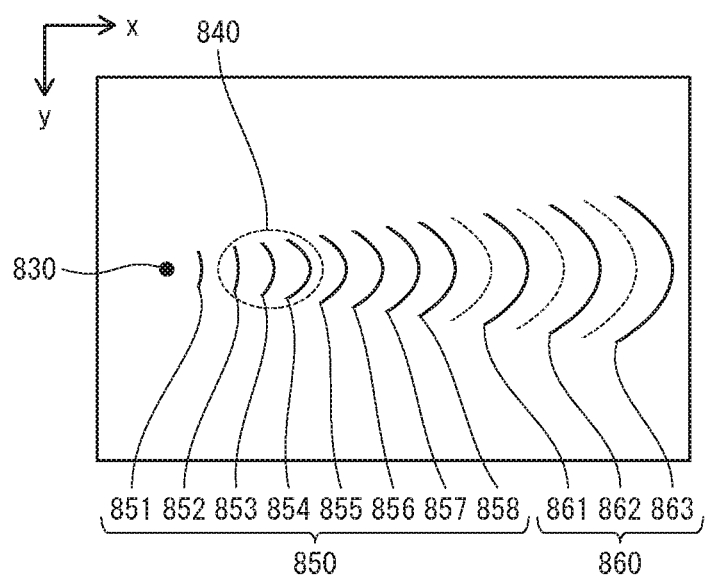
Figure 8C:
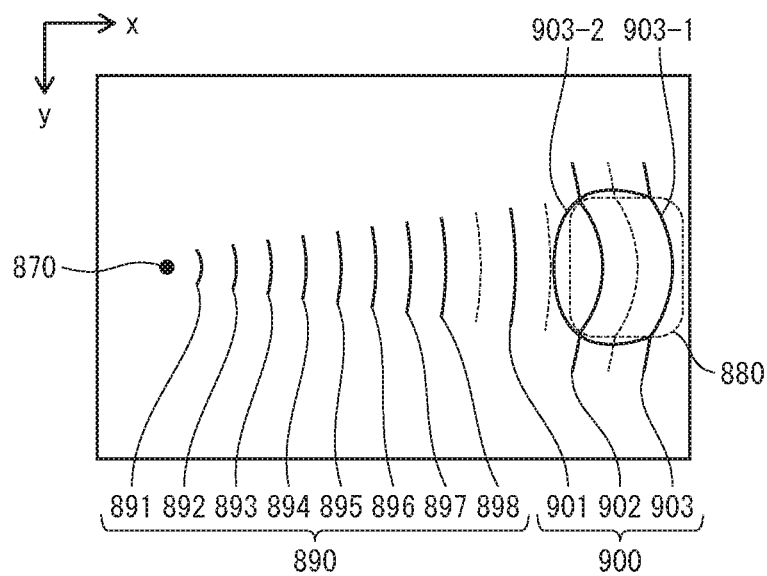

Description is provided of a case when shear wave propagation velocity changes at a part of the ROI, with reference to FIGS. 8A through 8C. FIG. 8A is a schematic illustrating a case when shear wave propagation velocity is lower at a belt-like area 812 extending in the element array direction (x-axis direction), than at surrounding areas 811 and 813. In this case, shear wave propagation velocity is high in area 812 and low in areas 811 and 813. Due to this, the analysis of propagation of the shear wave inside the entire area 812 can be performed by using only wavefronts 801 through 808 acquired during the first period P1. Thus, the analysis of propagation of the shear wave in the area 812 in which the shear wave has high propagation velocity can be performed with no decrease in temporal resolution, and thus, a decrease in accuracy of measurement of shear wave velocity can be suppressed. Meanwhile, the analysis of propagation of the shear wave in the areas 812 and 813 is performed by using wavefront 821 acquired during the second period P2, in addition to the wavefronts 801 through 808 acquired during the first period P1. However, because the propagation velocity of the shear wave is low in the areas 811 and 813, detection waves are transmitted at intervals short enough for accurate shear wave propagation analysis, and thus, a decrease in accuracy of measurement of shear wave velocity does not occur.

FIG. 8B is a schematic illustrating a case where a stiff tissue 840 (area in which propagation velocity of a shear wave is high) exists close to a push pulse focal point 830. In this case, a shear wave passes through and leaves the stiff tissue 840 during the first period P1. As such, the analysis of the propagation of the shear wave inside the tissue 840 can be performed by using only wavefront group 850 corresponding to the first period P1 (i.e., wavefronts 851 through 858). Due to this, the analysis of the propagation of the shear wave inside the tissue 840 can be performed using wavefronts acquired with the shortest transmission interval I1, and thus, a decrease in accuracy of measurement of shear wave velocity can be suppressed. Meanwhile, because the propagation velocity of the shear wave is not high outside the stiff tissue 840, the transmission interval I2 is short enough for performing accurate shear wave propagation analysis. Thus, the analysis of propagation of the shear wave outside the stiff tissue 840 can be performed with good accuracy using the wavefront group 850 corresponding to the first period P1 (i.e., wavefronts 851 through 858) and wavefront group 860 corresponding to the second period P2 (i.e., wavefronts 861 through 863).

Meanwhile, FIG. 8C is a schematic illustrating a case where a stiff tissue 880 exists far from a push pulse focal point 870. In this case, due to propagation velocity of a shear wave being low outside the stiff tissue 880, the wavefront of the shear wave does not reach the stiff tissue 880 during the first period P1, and reaches the stiff tissue 880 during the second period P2. Here, because the propagation velocity of the shear wave is not high outside the stiff tissue 880, the transmission interval I2 is short enough for performing the shear wave propagation analysis with good accuracy. Thus, the analysis of propagation of the shear wave outside the stiff tissue 880 can be performed using wavefront group 890 corresponding to the first period P1 (i.e., wavefronts 891 through 898) and wavefront group 900 corresponding to the second period P2 (i.e., wavefronts 901 through 903). Accordingly, a decrease in accuracy of measurement of shear wave velocity does not occur. Meanwhile, the analysis of the propagation of the shear wave inside the stiff tissue 880 is performed by using wavefront group 900 acquired with the transmission interval I2, although the propagation velocity of the shear wave is high in the stiff tissue 880. Due to this, a decrease in accuracy of the measurement of the propagation velocity occurs. However, when a stiff area is located at a great distance from a push pulse focal point, shear wave energy decays considerably before reaching the stiff area. Further, reflection of the shear wave occurs at the surface of the stiff area. Due to this, the wavefront 903 is divided into a reflected wave wavefront 903-2 and an incident wave wavefront 903-1, and further, the amount of displacement brought about by the reflected wave wavefront 903-2 is extremely small due to the shear wave having small energy. Accordingly, the analysis of propagation of the shear wave inside the stiff tissue 880 is difficult regardless of the detection wave transmission interval, and thus, the decrease in accuracy brought about by transmitting detection waves at the transmission interval I2 can be ignored.

In accordance with the transmission profile of detection waves pertaining to this embodiment, detection waves are transmitted at a short interval during a period temporally close to the time point of push pulse transmission in order to enable measuring shear waves with high velocity, and detection waves are transmitted at a long interval during a period temporally far from the time point of push pulse transmission in order to enable measuring shear waves with low velocity. Accordingly, the transmission intervals pertaining to this embodiment ensure that measurement of shear wave velocity is performed with good accuracy for any shear wave propagation velocity. Further, the interval at which detection waves are transmitted is longer than the transmission interval I1 outside the first period P1, and thus, heating of the ultrasound probe can be suppressed. Further, because the number of times detection signals are transmitted per unit time is reduced compared to when detection signals are always transmitted at the transmission interval I1, the amount of receive signals can be reduced and processing amount can be accordingly reduced.

Further, the reduction of processing amount enables reducing the amount of time between the transmission of a push pulse and the generation of an elasticity image, which contributes to improvement of real-time performance and usability of the ultrasound diagnostic device.

Summary

The structure of the ultrasound diagnostic device pertaining to this embodiment enables reducing the frequency of transmission/reception of detection waves while suppressing a decrease in accuracy of measurement of shear wave velocity.

Embodiment 2

Embodiment 1 describes a case where the frequency of transmission/reception of detection waves is reduced by using a detection wave transmission profile that is prepared beforehand.

Meanwhile, embodiment 2 is characterized for optimizing the detection wave transmission profile based on information indicating tissue stiffness having been acquired in advance.

Operations

Figure 9:
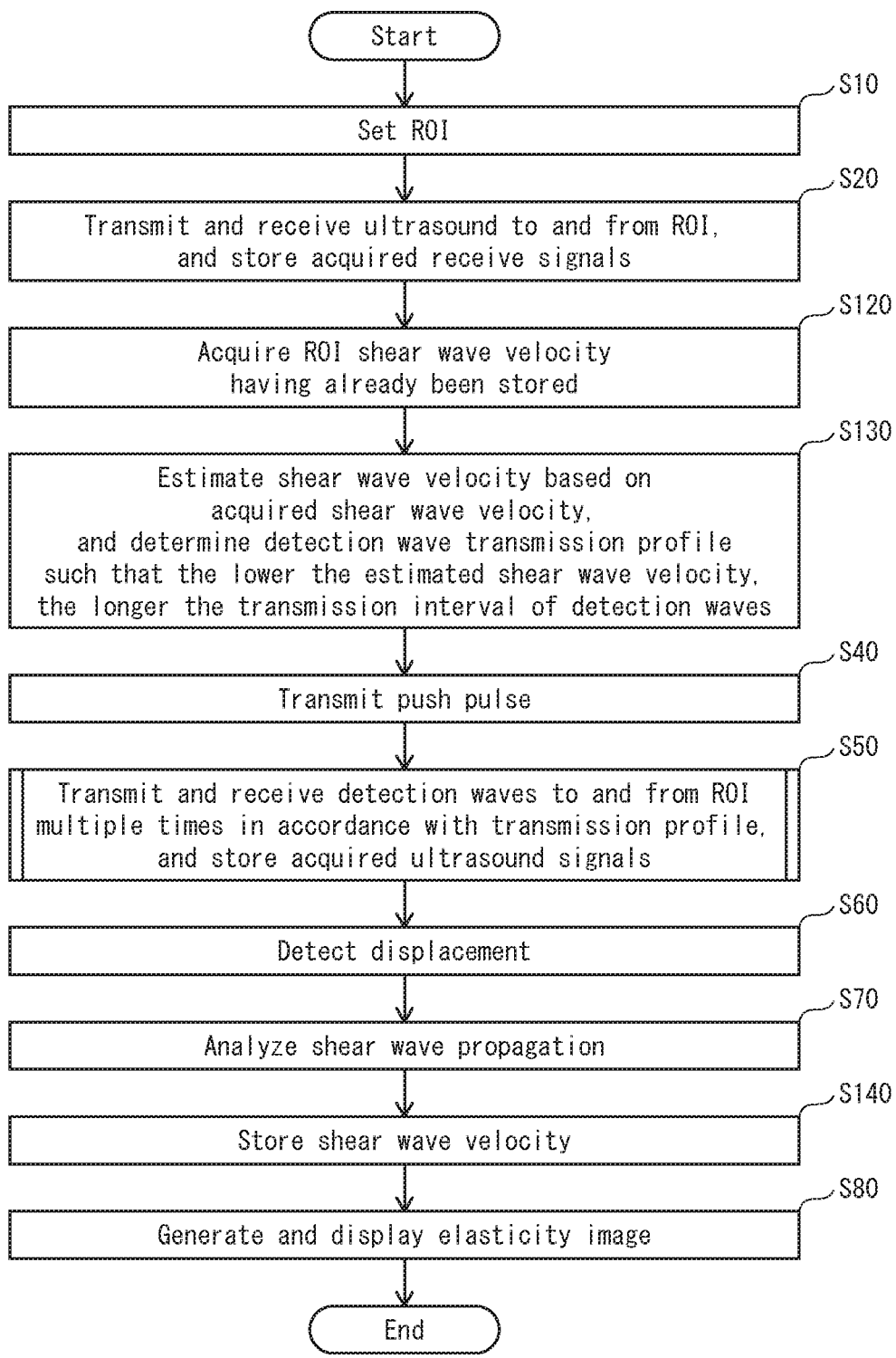
FIG. 9 is a flowchart illustrating operations of an ultrasound diagnostic device pertaining to embodiment 2.

The following describes operations of an ultrasound diagnostic device pertaining to embodiment 2. FIG. 9 is a flowchart illustrating the operations of the ultrasound diagnostic device pertaining to embodiment 2. Note that in the following, operations that are illustrated in FIG. 2 are provided with the same step numbers and are not described in detail.

In the ultrasound diagnostic device pertaining to embodiment 2, the result of propagation analysis that the propagation analyzer performs in Step S70 is stored to the elasticity image storage in Step S140. Further, in Step S120, the ultrasound signal acquirer acquires the propagation analysis result having been stored in Step S140 performed in the past for the same ROI. In Step S130, shear wave velocity is estimated from the propagation analysis result, and the detection wave transmission profile is determined so that detection waves are transmitted at a short interval during a period where shear wave velocity is expected to be high and are transmitted at a long interval during a period where shear wave velocity is expected to be low.

The following describes Step S130 in detail.

Figure 10:
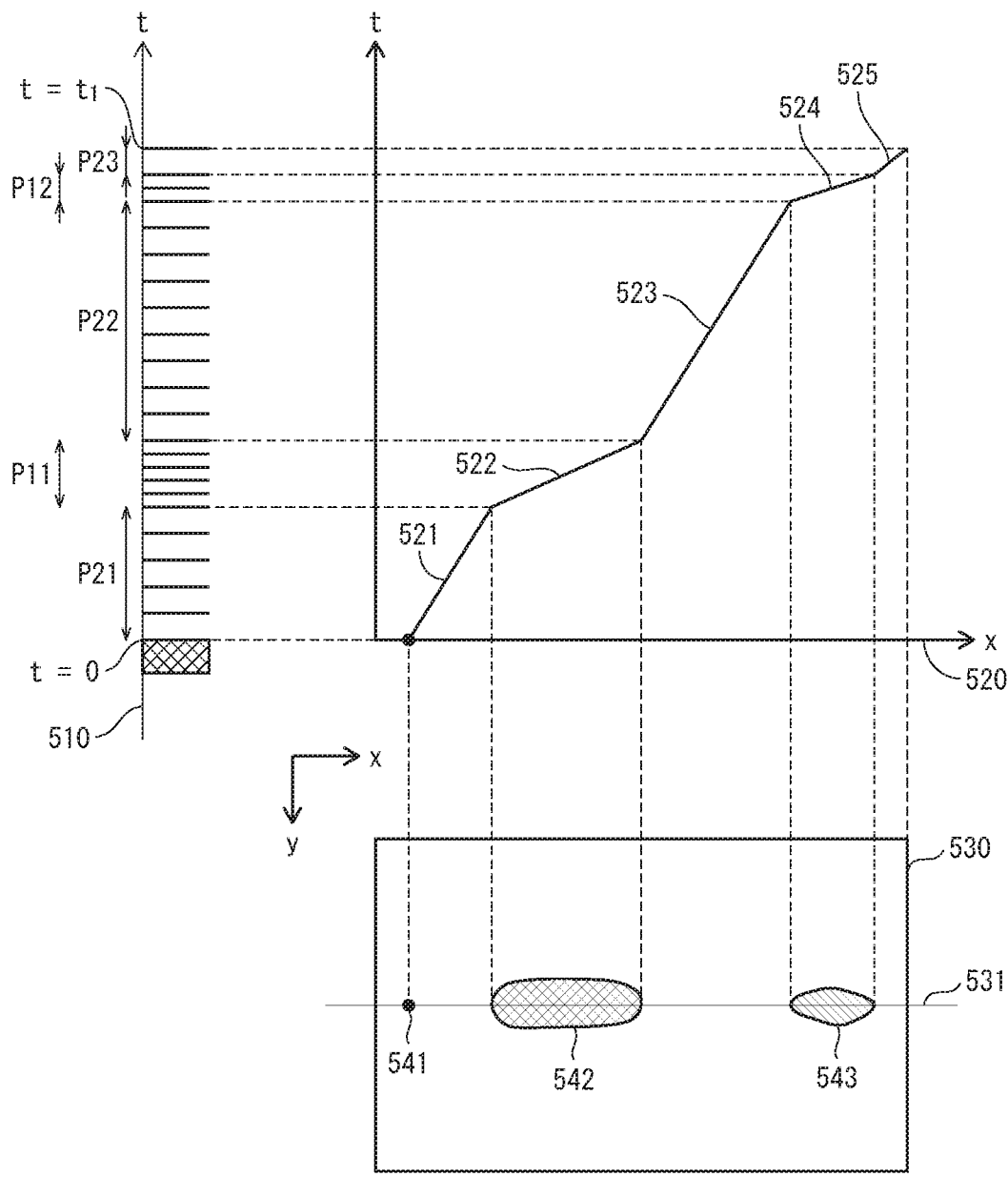
FIG. 10 is a schematic illustrating a transmission profile determination method pertaining to embodiment 2.

First, the ultrasound signal acquirer acquires an elasticity image acquired in the past for the ROI from the elasticity image storage. Subsequently, a detection wave transmission profile is determined based on the elasticity image. FIG. 10 is a schematic illustrating a transmission profile determination method pertaining to embodiment 2. In FIG. 10, elasticity image 530 is an elasticity image for a ROI. Here, inclusions 542 and 543 are stiffer than surrounding tissues.

Focal point 541 indicates a push pulse focal point having been used in acquiring the elasticity image. Velocity graph 520 is a graph showing shear wave velocity along a straight line 531 at a predetermined depth where the push pulse focal point 541 is located. As shown by the velocity graph 520, shear wave velocity is high at sections 522 and 524 respectively corresponding to the inclusions 542 and 543, and is low at the other sections 521, 523, and 525. Here, estimation of shear wave velocity is performed by assuming that shear wave velocity is the same as that in the elasticity image 530, and the detection wave transmission profile is determined so that detection waves are transmitted temporally densely during a period where shear wave velocity is expected to be high and a long transmission interval is set for other periods. That is, a detection wave transmission profile 510 as described in the following is generated. A short detection wave transmission interval is set for periods P11 and P12 respectively corresponding to the sections 522 and 524 where shear wave velocity is high. Meanwhile, a long detection wave transmission interval is set for periods P21, P22, and P23 respectively corresponding to the sections 521, 523, and 525 where shear wave velocity is low. Specifically, a transmission interval of 100 µs is set when shear wave velocity is expected to be no lower than a predetermined threshold (for example, 5 m/s), and a transmission interval of 200 µs is set when shear wave velocity is expected to be lower than the predetermined threshold.

Further, a configuration may be made so that after time point $t_1$ when the shear wave is expected to reach the edge of the ROI, detection waves are not transmitted. This prevents transmission/reception of unnecessary detection waves after the shear wave leaves the ROI, and thus further reduces the number of times detection waves are transmitted/received.

Supplement

In the above, description is provided of a case where the position of the push pulse focal point remains the same between a measurement of the ROI having been performed to generate the elasticity image stored in the elasticity image storage (referred to in the following as a previous measurement) and a measurement of the ROI to be newly performed (referred to in the following as a new measurement). However, for example, the position of the push pulse focal point for the new measurement may differ from that for the pervious measurement. In this case, processing as described in the following can be performed.

For example, when the position of the push pulse focal point for the previous measurement and the position of the push pulse focal point for the new measurement are the same in the depth direction (y-axis direction) and differ in only the element array direction (i.e., x-axis direction), the t coordinate of the new push pulse focal point in the velocity graph is set as t=0 (time point immediately following push pulse transmission) in the detection wave transmission profile. Specifically, when shear wave travel direction is the right direction (the x-axis positive direction) and the new push pulse focal point is located at the right side (in the x-axis positive direction) from the previous push pulse focal point, t=0 in the detection wave transmission profile is moved in the t-axis positive direction so that the time point when shear wave is expected to pass the new push pulse focal point becomes t=0 (time point immediately following push pulse transmission). Similarly, when the push pulse focal point moves in a direction opposite the shear wave travel direction, t=0 in the detection wave transmission profile is moved in the t-axis negative direction so that the time point when shear wave is expected to pass the new push pulse focal point becomes t=0.

Further, when the position of the push pulse focal point for the previous measurement and the position of the push pulse focal point for the new measurement have different depths, shear wave velocity at the depth of the position of the new push pulse focal point may be used for determining the detection wave transmission profile. Alternatively, shear wave velocity at the depth of the position of the previous push pulse focal point may be used in place of shear wave velocity at the depth of the position of the new push pulse focal point.

Further, shear wave velocity need not be that at a depth of the position of a push pulse focal point, and shear wave propagation velocity at a certain depth, such as a depth including a center of the ROI or a certain depth from a skin surface, may be used. For example, in the example described above, the straight line 531 may be set at a depth corresponding to a center of the ROI in the depth direction. Further, shear wave propagation velocity may be estimated by detecting shear wave propagation velocity at each of a plurality of lines in the elasticity image 530 each corresponding to a different depth, and combining the shear wave propagation velocities so detected. Here, the lines each corresponding to a single depth may, for example, be a combination of a straight line splitting the ROI at a 1:3 ratio in the depth direction, a straight line splitting the ROI at a 1:1 ratio in the depth direction, and a straight line splitting the ROI at a 3:1 ratio in the depth direction. The combining may be performed, for example, by using an average of shear wave propagation velocities at different y coordinates, for each coordinate in the element array direction (x-axis direction). Alternatively, other representative values, such as a median or a maximum, may be used in place of an average.

Further, in the description provided above, shear wave velocity is calculated based on an elasticity image. However, shear wave velocity may be calculated based on a propagation analysis result. Further, shear wave velocity may be calculated, for example, by using a method of assuming a time point when displacement is first detected following push pulse transmission as wavefront arrival time.

Further, when shear wave velocity at the ROI has not yet been acquired, the ultrasound signal acquirer may set the detection wave transmission profile according to the method pertaining to embodiment 1.

Summary

By setting the detection wave transmission profile as described above, detection waves can be transmitted temporally densely during a period where shear wave velocity is expected to be high, whereby a decrease in accuracy of measurement of shear wave velocity can be suppressed. Further, because a long detection wave transmission interval is set for a period where shear wave velocity is expected to be low, heating of the ultrasound probe can be suppressed. Further, because the number of times detection waves are transmitted is reduced compared to when detection waves are always transmitted temporally densely, the amount of receive signals can be reduced and processing amount can be reduced. Further, because processing amount can be reduced and the transmission/reception of unnecessary detection waves can be suppressed, the amount of time between push pulse transmission and the generation of an elasticity image can be reduced, which contributes to improvement of real-time performance and usability of the ultrasound diagnostic device.

Embodiment 3

In embodiments 1 and 2, push pulse transmission is performed only once in the calculation of shear wave velocity.

Meanwhile, embodiment 3 is characterized for the calculation of shear wave velocity being performed with push pulse transmission performed multiple times.

Operations

Figure 11:
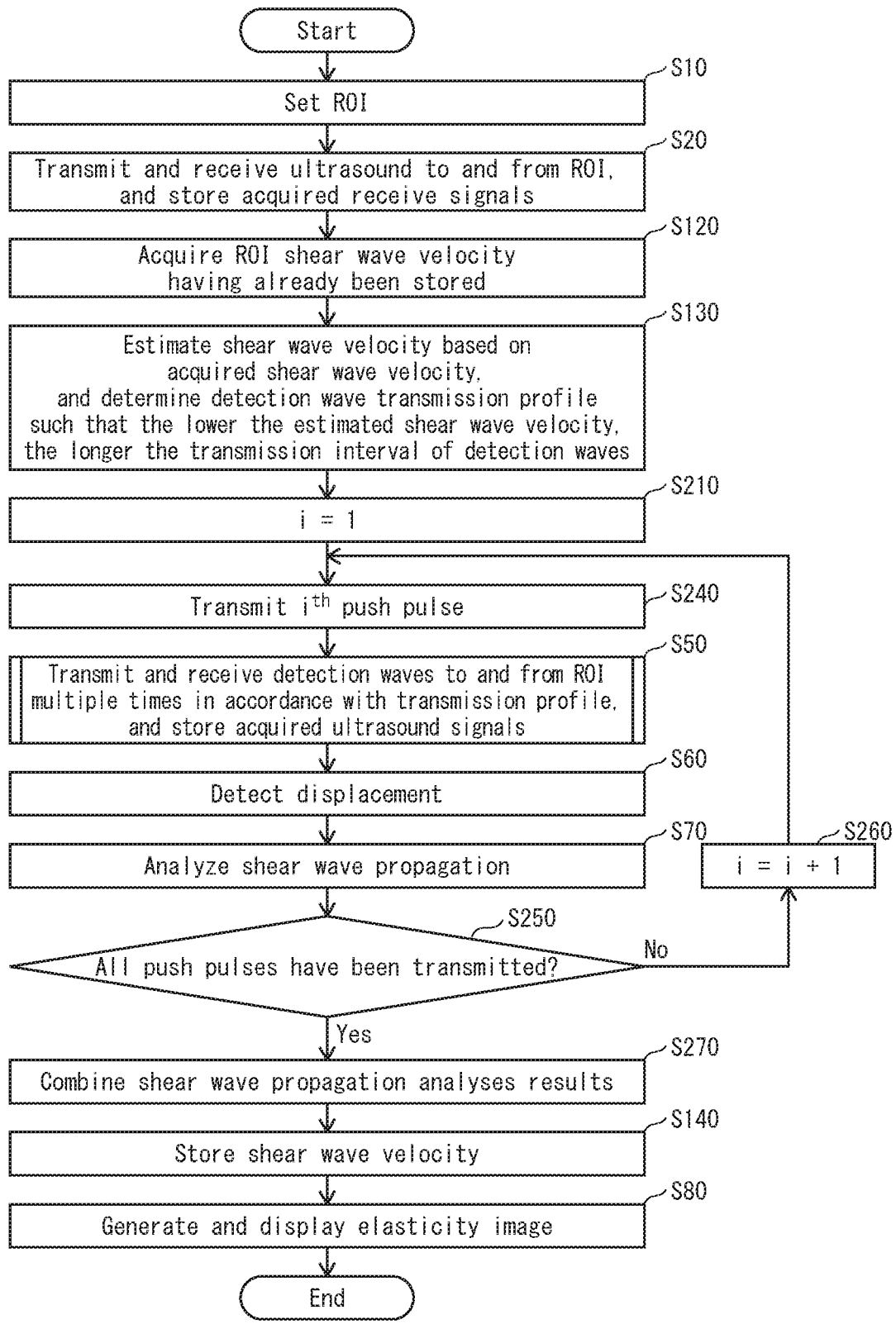
FIG. 11 is a flowchart illustrating operations of an ultrasound diagnostic device pertaining to embodiment 3.
Figure 12:
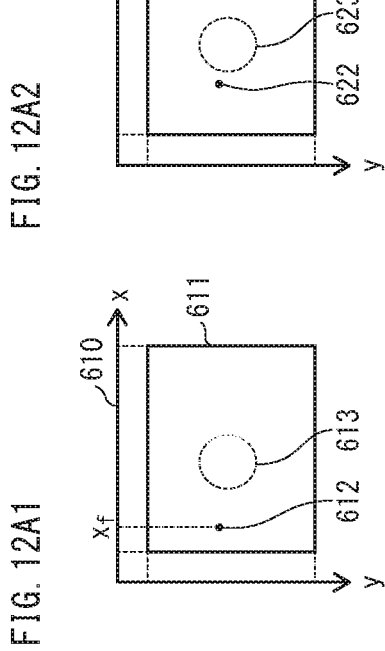

The following describes operations of an ultrasound diagnostic device pertaining to embodiment 3. FIG. 11 is a flowchart illustrating the operations of the ultrasound diagnostic device pertaining to embodiment 3. Note that in the following, operations that are illustrated in FIGS. 2 and 9 are provided with the same step numbers and are not described in detail.

The operations from the setting of the ROI (Step S10) to the determination of the detection wave transmission profile (Step S130) are the same as those in embodiment 2. Thus, such operations are not described in the following.

The following describes push pulse transmission and subsequent transmission/reception of detection waves (Steps S210 to S250). Here, four push pulse focal points are used, and transmission/reception of detection waves and subsequent propagation analysis is performed following the transmission of each push pulse. Here, the positions of the four focal points are each set at a center of a sub-area acquired by splitting the ROI in four in the element array direction. Further, transmission/reception of detection waves in accordance with the transmission profile determined in Step S130, the detection of displacement, and shear wave propagation analysis are performed following the transmission of each push pulse.

The following describes combining (Step S270) of shear wave propagation analyses results, with reference to schematic FIGS. 12A1, 12A2, 12A3, 12A4, 12B, and 12C. FIG. 12A1, FIG. 12A2, FIG. 12A3, and FIG. 12A4 respectively correspond to a first push pulse, a second push pulse, a third push pulse, and a fourth push pulse. Each of these drawings illustrates the positional relationship between a ROI, shear wave velocity distribution, and push pulse focal point. For example, in velocity distribution diagram 610 in FIG. 12A1, push pulse focal point 612 is located near the left end of ROI 611, and area 613 where shear wave propagation velocity is high is detected. Similarly, in velocity distribution diagram 620 in FIG. 12A2, push pulse focal point 622 is located at the left side of ROI 621, and area 623 where shear wave propagation velocity is high is detected. Further, in velocity distribution diagram 630 in FIG. 12A3, push pulse focal point 632 is located at the right side of ROI 631, and area 633 where shear wave propagation velocity is high is detected. Similarly, in velocity distribution diagram 640 in FIG. 12A4, push pulse focal point 642 is located near the right end of ROI 641, and area 643 where shear wave propagation velocity is high is detected. The areas 613, 623, 633, and 643 where shear wave propagation velocity is high actually correspond to a same single tissue. Here, it should be noted that while a boundary between such an area and other areas is clear at a portion close to the position of a push pulse focal point, the boundary may not be clear at a portion far from the position of a push pulse focal point due shear wave decay. The velocity distribution diagrams 610, 620, 630, and 640 are combined to generate a single velocity distribution diagram such as that illustrated in FIG. 12B. Specifically, for each coordinate position, shear wave velocity is acquired from each of the velocity distribution diagrams 610, 620, 630, and 640, and a representative value is calculated. The calculation of the representative value may be performed, for example, by using weighted average, maximum, or the like. Alternatively, the calculation may be performed by using an average from which invalid data (for example, data from a velocity distribution diagram that does not include a value for the coordinate position due to velocity not being acquired, or data from a velocity distribution diagram that differs greatly from the velocities acquired from the rest of the velocity distribution diagrams) is excluded. When using weighted average, a value that becomes greater as the distance from the position of the push pulse focal point decreases and becomes smaller as the distance from the position of the push pulse focal point increases may be used as a weighting factor This is because the closer to the push pulse focal point, the greater the shear wave energy and thus the higher the accuracy of the shear wave velocity measurement is expected to be. For example, the weighting factor a, may be set to equal zero when the difference between the position of the push pulse focal point (x coordinate ($x_f$)) and an x coordinate of processing-target data is equal to or greater than a predetermined threshold as shown by weighting factor 661 in FIG. 12C. Further, as the weighting factor $a_i$, any function may be used whose value increases as the difference between the position of the push pulse focal point (x coordinate ($x_f$)) and the x coordinate of processing-target data decreases, as shown by weighting factors 662, 663, and 664 in FIG. 12C. By making such a configuration, a velocity distribution diagram 650 can be generated that reveals the full picture of area 653 where shear wave propagation velocity is high.

Following the combining of the shear wave propagation analyses results, the propagation analyzer holds the velocity distribution diagram 650 acquired through the combining (Step S140), an elasticity image is generated, and the controller displays this elasticity image on the display (Step S80).

Summary

With the configuration described above, the distance between each measurement point in the ROI and the closest push pulse focal point can be reduced, and thus the measurement of shear wave velocity can be performed with high accuracy. Further, detection waves are transmitted temporally densely during a period where shear wave velocity is high, and a decrease in accuracy of measurement of shear wave velocity is suppressed. Further, a long detection wave transmission interval is set for a period where shear wave velocity is low, and heating of the ultrasound probe is suppressed. Further, due to the number of times detection waves are transmitted being reduced, the amount of receive signals can be reduced and processing amount can be reduced. Further, due to processing amount being reduced, the amount of time from push pulse transmission to the generation of an elasticity image is reduced, which contributes to improvement of real-time performance and usability of the ultrasound diagnostic device.

Modification of Embodiment 3

In embodiment 3, description is provided of a case where shear wave propagation analyses results for multiple push pulses are combined, and in the subsequent measurements, the combined results are used for optimizing the transmission/reception of detection waves.

Meanwhile, the present modification is characterized in that measurement results for multiple push pulses are combined, and that a shear wave propagation analysis result for one push pulse is used for detection wave transmission performed following the transmission of subsequent push pulses.

Operations

Figure 13:
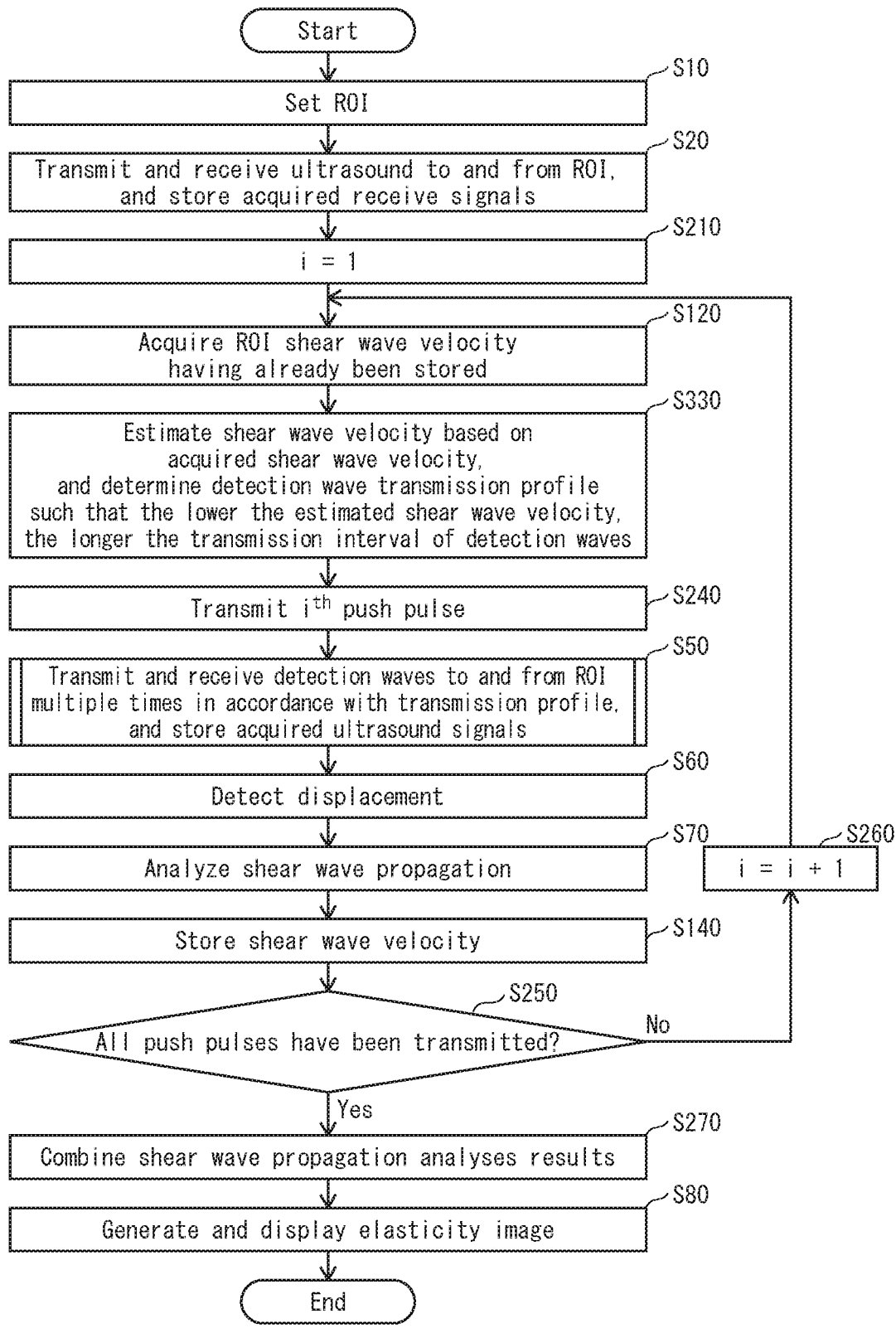
FIG. 13 is a flowchart illustrating operations of an ultrasound diagnostic device pertaining to a modification of embodiment 3.

The following describes operations of an ultrasound diagnostic device pertaining to the modification. FIG. 13 is a flowchart illustrating the operations of the ultrasound diagnostic device pertaining to the modification. Note that in the following, operations that are illustrated in FIGS. 2, 9, and 11 are provided with the same step numbers and are not described in detail.

This modification differs from embodiment 3 in that for each transmission of a push pulse, a propagation analysis result having been stored in Step S140 is acquired (Step S120) and a detection wave transmission profile is determined (Step S330). Further, each time propagation analysis pertaining to one push pulse is completed, the propagation analyzer holds the result of the propagation analysis (Step S140). Thus, in Step S120 for i≥2, the shear wave propagation analysis result having been stored in Step S140 for i=(i−1) is acquired. Further, after propagation analyses for all push pulses are completed, combining of the shear wave propagation analyses results (Step 5270) and generation and displaying of an elasticity image (Step S80) are performed.

The following describes Step S330 in detail.

Figure 14:
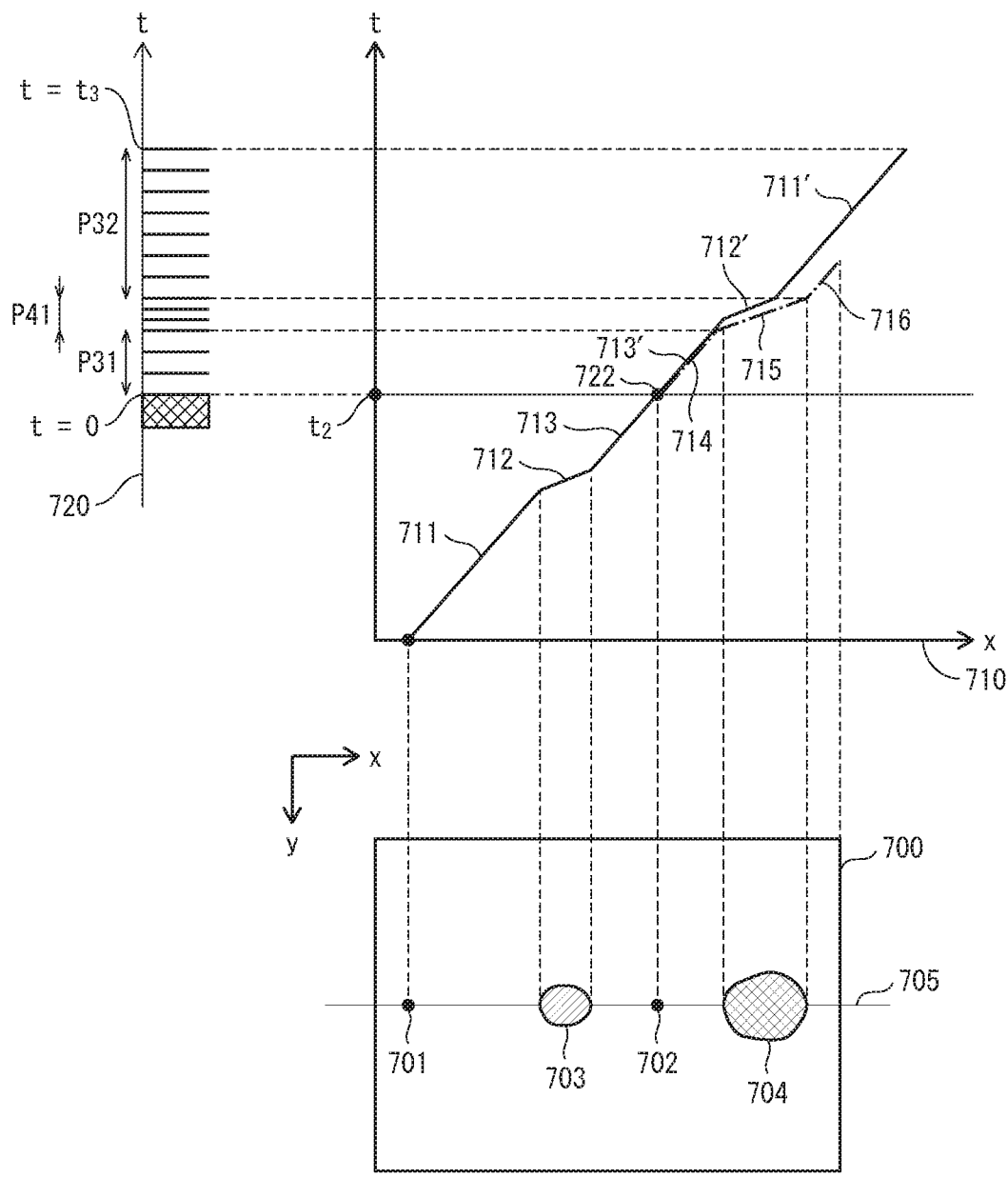
FIG. 14 is a schematic illustrating a transmission profile determination method pertaining to the modification of embodiment 3.

First, the ultrasound signal acquirer acquires, from the elasticity image storage, an elasticity image for the ROI pertaining to a most previously transmitted push pulse. Subsequently, a detection wave transmission profile is determined based on the elasticity image. FIG. 14 is a schematic illustrating a transmission profile determination method pertaining to the modification. Elasticity image 700 in FIG. 14 is an elasticity image for a ROI pertaining to a first push pulse. Here, inclusion 703 is stiffer than surrounding tissues and inclusion 704 is even stiffer than inclusion 703. Further, focal point 701 is a focal point of the first push pulse. Velocity graph 710 is a graph showing shear wave velocity along a straight line 705 at a predetermined depth where the focal point 701 of the first push pulse and focal point 702 of a second push pulse are located. As shown by the velocity graph 710, shear wave velocity is high at section 722 corresponding to inclusion 703, is even higher at section 715 corresponding to inclusion 704, and is low at the other sections 711, 714, 713, and 716. Detection waves are transmitted temporally densely during a period where shear wave velocity is high and a longer detection wave transmission interval is set for other periods. Here, because the positions of focal points differ, estimation of shear wave velocity is performed according to the following method. First, so that t=0 holds true at the timing when the transmission of the second push pulse is completed, time point t2 at which a shear wave generated by the first push pulse arrives at focal point 702 is set to t=0 (time point when transmission of the second push pulse is completed) in transmission profile 720. Then, correction of data is performed for an area where shear wave travel direction reverses due to the positions of the focal points differing. Specifically, within the area between focal points 701 and 702, a shear wave generated at focal point 701 travels towards the right (x-axis positive direction) whereas a shear wave generated at focal point 702 travels towards the left (x-axis negative direction). Here, an assumption is made that the magnitude (absolute value) of shear wave propagation velocity is not dependent upon travel direction in this area. Specifically, sections 711, 712, and 713 corresponding to the area located towards the focal point 701 from the focal point 702 (the area at the left side of focal point 702) are inverted through point 722 in the velocity graph 710 to respectively yield sections 711', 712', and 713'. Further, a short detection wave transmission interval is set for a period corresponding to a section where shear wave velocity is high, and a long detection wave transmission interval is set for a period corresponding to a section where shear wave velocity is low. As such, a short detection wave transmission interval is set for period P41, which corresponds to at least one of sections 715 and 712', and a long detection wave transmission interval is set for the other periods P31 and P32. Further, following time point $t_3$ after which shear waves are expected to be no longer present in the ROI even when considering the inverted sections 711', 712', and 713', detection waves are not transmitted.

Summary

The configuration described above is an addition to the configuration pertaining to embodiment 3, and enables, when performing push pulse transmission multiple times, optimizing the detection wave transmission profile for the second and subsequent push pulses even if shear wave velocity in the ROI is not acquired beforehand.

Other Modifications pertaining to Embodiments (1) In embodiment 1, description is provided of a case where the lengths of the first period P1, the second period P2, the third period P3, and the fourth period P4 are 3.8 ms, 3.8 ms, 11.2 ms, and 12 ms, respectively, and the lengths of the transmission interval I1, the transmission interval I2, the transmission interval I3, and the transmission interval I4 are 100 μs, 200 μs, 400 μs, and 800 μs, respectively. However, the present invention is not limited to this case. Specifically, the periods P1 through P4 may each have any length, and the transmission intervals I1 through I4 suffice as long as they satisfy I1<I2<I3<I4. For example, the transmission intervals I1 through I4 may be set to satisfy I1:I2:I3:I4=1:2:3:4 or I1:I2:I3:I4=1:3:9:27. Meanwhile, it is preferable that the transmission interval I1 be an interval allowing propagation analysis of a shear wave having a highest propagation velocity vi to be performed with good accuracy. Further, it is preferable that P1 be an amount of time from generation of a shear wave having the highest propagation velocity $v_1$ until the shear wave leaves a ROI. Further, it is preferable that the transmission interval I2 be an interval allowing propagation analysis of a shear wave having a second highest propagation velocity $v_2$ to be performed with good accuracy. Further, it is preferable that P1+P2 be an amount of time from generation of a shear wave having the propagation velocity $v_2$ until the shear wave leaves a ROI. Similarly, it is preferable that the transmission interval I4 be an interval allowing propagation analysis of a shear wave having a lowest propagation velocity $v_4$ to be performed with good accuracy. Further, it is preferable that P1+P2+P3+P4 be an amount of time from generation of a shear wave having the propagation velocity $v_4$ until the shear wave leaves a ROI.

In the embodiments and the modification described above, four periods and four transmission intervals are set. However, the number of periods and transmission intervals that are set is not limited to four, and may be two, three, or five or more.

Further, a modification may be made so that depending upon ROI size, the examination-target part, and/or the like, profile adjustment is performed and/or selection of one among multiple profiles prepared beforehand is performed. For example, in a case of a ROI having great width in the element array direction, the number of times push pulses are transmitted can be reduced by using a technique such as extending each of transmission intervals I2 through I4. Further, for example, each of the transmission intervals I1 through I4 may be shortened for a ROI having high average elasticity, whereas each of the transmission intervals I1 through I4 may be extended for a ROI having low average elasticity.

(2) In the embodiments and the modification, a detection wave transmission interval is defined by using pairs of a transmission interval and a time period. Alternatively, a transmission profile may be defined by using pairs of a transmission interval and a transmission count. For example, a transmission profile defined by a first period P1 of 3.8 ms, a transmission interval I1 of 100 μs, a second period P2 of 3.8 ms, a transmission interval I2 of 200 μs, a third period P3 of 11.2 ms, a transmission interval I3 of 400 μs, a fourth period P4 of 12 ms, and a transmission interval I4 of 800 μs may also be defined by a first transmission count C1 of 38 transmissions, a transmission interval I1 of 100 μs, a second transmission count C2 of 19 transmissions, a transmission interval I2 of 200 μs, a third transmission count C3 of 28 transmissions, a transmission interval I3 of 400 μs, and a fourth transmission count C4 of 15 transmissions, and a transmission interval I4 of 800 μs. These two transmission profiles are substantially the same, and they differ for being expressed in different ways. Naturally, a detection wave transmission profile may also be defined by using pairs of a transmission period and a transmission count.

(3) In the embodiments and the modification, a transmission profile is defined by setting a transmission interval for each period and changing the transmission interval in levels. However, the transmission interval may be set to change continuously. For example, in the case described in embodiment 1, the transmission interval may be defined as a function increasing in accordance with the time amount between push pulse transmission and transmission of a previous detection wave (e.g., a linear function). Similarly, in the case described in embodiment 2 for example, the transmission interval may be defined as a function decreasing as estimated shear wave velocity increases (e.g., an inversely proportional function).

(4) In embodiments 2 and 3 and the modification, detection waves are no longer transmitted at time points when shear wave wavefronts are expected to be outside the ROI. Further, the following processing may be additionally performed. For example, processing of extending the first period P1 or reducing the transmission interval I1 may be performed when the total number of detection wave transmissions is smaller than a predetermined threshold. Specifically, the first period P1 may be extended so that the total number of detection wave transmissions equals 100, when the total number of detection wave transmissions does not reach 80. By making such a modification when there is no need to consider the heating of the ultrasound probe due to the total number of detection wave transmissions being relatively small, the accuracy of shear wave propagation analysis can be further improved.

(5) In the embodiments and the modification, shear wave propagation analysis is performed through extraction of displacement areas, thinning, spatial filtering, and temporal filtering, performed in this order. Alternatively, shear wave propagation analysis can be performed through detection of time points where maximum displacement is observed at different areas, temporal filtering, and spatial filtering, performed in this order.

Instead of performing shear wave propagation analysis according to the above-described methods, shear value propagation analysis may be simply performed regarding the time point at which displacement is initially observed at each area following pulse transmission as the time point when a shear wave wavefront has reached the area.

(6) In the modification of embodiment 3, the determination of a detection wave transmission profile pertaining to a push pulse for i=1 is performed according to the method described in embodiment 1. Alternatively, the detection wave transmission profile for such a push pulse may be determined according to the method described in embodiment 3. Further, a detection wave transmission profile pertaining to a push pulse for i≥2 is determined by using a shear value propagation analysis result pertaining to the most-previously transmitted push pulse. Alternatively, for example, the detection wave transmission profile for such a push pulse may be determined by using a shear value propagation analysis result pertaining to a second-to-most-previously-transmitted push pulse or a push pulse transmitted before such push pulse.

(7) In the embodiments and the modification of embodiment 3, the ultrasound diagnostic device 1 is connectable to the display 3. However, the ultrasound diagnostic device 1 need not be connectable to the display 3. For example, the ultrasound diagnostic device 1 may include the display 3. Alternatively, a modification may also be made such that the ultrasound diagnostic device 1 is not connected to the display 3, and stores elasticity images having been generated and stored to the elasticity image storage 19 by the propagation analyzer 15 to a different storage medium or outputs such elasticity images to another device over a network.

Similarly, the ultrasound diagnostic device 1 may include the ultrasound probe 2. Alternatively, the ultrasound probe 2 may include the ultrasound signal acquirer 13 and a ultrasound diagnostic device not including the ultrasound signal acquirer 13 may acquire acoustic line signals from the ultrasound probe 2.

(8) All or some of the constituent elements of the ultrasound diagnostic devices pertaining to the embodiments and the modifications may be implemented as one or more chips of integrated circuits, may be implemented as a computer program, or may be implemented in any other form. For example, a modification may be made of implementing the displacement detector and the propagation analyzer as a single chip, or a modification may be made of implementing the ultrasound signal acquirer on one chip and implementing the displacement detector and other constituent elements on another chip.

Implementation with an integrated circuit is typically achieved by using a large scale integration (LSI). An LSI may be referred to as an integrated circuit, a system LSI, a super LSI, or an ultra LSI may be used depending on the level of integration.

Further, techniques of circuit integration are not limited to LSI, and implementation may be achieved by a dedicated circuit or general-purpose processor. Further, a field programmable gate array (FPGA) that is programmable after LSI manufacture or a reconfigurable processor, in which circuit cell connections and settings in the LSI can be reconfigured after LSI manufacture may be used.

Further, if a circuit integration technology is introduced that replaces LSI due to advances in semiconductor technology or another derivative technology, such technology may of course be used to integrate the functional blocks.

Further, the ultrasound diagnostic devices pertaining to the embodiments and modifications may be implemented as a program stored on a storage medium and a computer that reads and executes the program. The storage medium may be any kind of storage medium, such as a memory card or CD-ROM. Further, the ultrasound diagnostic device pertaining to the present invention may be implemented as program downloadable via a network and a computer that downloads and executes the program.

(9) The above embodiments each describe a preferable and specific example of the present invention. The values, shapes, materials, constituent elements, positions and connections of the constituent elements, processes, ordering of processes, etc., are only examples and are not intended to limit the scope of the present invention. Further, among the constituent elements described in the embodiments, processes not recited in the independent claims that indicate highest level concepts of the present invention are described as optional elements constituting a preferable form.

Further, in order to aid understanding of the invention, the dimensions of the constituent elements illustrated in the drawings referred to in the embodiments may differ from actual dimensions. Further, the present invention is not intended to be limited in scope by the description in the embodiments, and can be appropriately modified so as not to depart from the scope of the present invention.

Further, in ultrasound diagnostic devices are members such as circuit elements and lead lines on substrates, but description thereof is omitted, as various forms of implementation of electrical wiring and circuitry are possible based on common knowledge in the technical fields, and such description is not directly relevant to the present invention. The drawings referred to above are schematics, and are not necessarily exact.

Supplement (1) One aspect of the present invention is an ultrasound diagnostic device that uses an ultrasound probe to detect a propagation velocity of a shear wave generated at a specific part inside a subject by physically pushing tissue at the specific part by transmitting an ultrasound push pulse focusing on the specific part and then repeatedly transmitting and receiving ultrasound detection waves to and from inside the subject, the ultrasound diagnostic device including: ultrasound signal processing circuitry, the ultrasound signal processing circuitry including: a push pulse transmitter that transmits a push pulse towards the subject; a detection wave transmitter/receiver that, following the transmission of the push pulse, transmits plane wave transmission detection waves towards a region of interest (ROI) inside the subject and receives reflection detection waves corresponding to the transmission detection waves from the subject, to generate receive signals sequentially; a displacement detector that detects, from the receive signals, subject tissue displacement occurring inside the ROI at time points of reception of the reflection detection waves due to a shear wave generated by the push pulse; and a shear wave analyzer that detects a shear wave propagation velocity inside the ROI based on the subject tissue displacement, wherein the transmission detection waves at least include transmission detection waves transmitted by the detection wave transmitter/receiver at a first transmission interval and transmission detection waves transmitted by the detection wave transmitter/receiver at a second transmission interval longer than the first transmission interval.

Another aspect of the present invention is an ultrasound signal processing method in which an ultrasound probe is used to detect a propagation velocity of a shear wave generated at a specific part inside a subject by physically pushing tissue at the specific part by transmitting an ultrasound push pulse focusing on the specific part and then repeatedly transmitting and receiving ultrasound detection waves to and from inside the subject, the ultrasound signal processing method including: transmitting a push pulse towards the subject; following the transmission of the push pulse, transmitting plane wave transmission detection waves towards a region of interest (ROI) inside the subject and receiving reflection detection waves corresponding to the transmission detection waves from the subject, to generate receive signals sequentially; detecting, from the receive signals, subject tissue displacement occurring inside the ROI at time points of reception of the reflection detection waves due to a shear wave generated by the push pulse; and detecting a shear wave propagation velocity inside the ROI based on the subject tissue displacement, wherein the transmission detection waves at least include transmission detection waves transmitted at a first transmission interval and transmission detection waves transmitted at a second transmission interval longer than the first transmission interval.

The ultrasound diagnostic device and the ultrasound signal processing method, each of which pertaining to one aspect of the present invention, optimize an interval at which detection waves are transmitted to reduce the frequency at which detection waves are transmitted/received, while suppressing a decrease in accuracy of measurement of shear wave propagation velocity.

(2) The ultrasound diagnostic device of (1) may be modified such that the detection wave transmitter/receiver transmits transmission detection waves at the first transmission interval for a predetermined period from the transmission of the push pulse and transmits transmission detection waves at the second transmission interval after elapse of the predetermined period.

(3) The ultrasound diagnostic device of (1) may be modified such that the detection wave transmitter/receiver transmits transmission detection waves at the first transmission interval until a total number of transmission detection waves transmitted since the transmission of the push pulse reaches a predetermined number and transmits transmission detection waves at the second transmission interval after the total number of transmission detection waves transmitted reaches the predetermined number.

According to modifications (2) and (3) above, detection waves are transmitted at a short interval during a period temporally close to the time point of push pulse transmission in order to enable measuring shear waves with high velocity, and detection waves are transmitted at a long interval during a period temporally far from the time point of push pulse transmission in order to enable measuring shear waves with low velocity. Accordingly, it is ensured that measurement of shear wave velocity is performed with good accuracy for any shear wave propagation velocity.

(4) The ultrasound diagnostic device of (1) may be modified such that the shear wave analyzer holds the shear wave propagation velocity, and the detection wave transmitter/receiver, before transmission of a subsequent push pulse, estimates a shear wave propagation velocity based on the shear wave propagation velocity held by the shear wave analyzer, and after the transmission of the subsequent push pulse, transmits transmission detection waves at the first transmission interval during a period over which the estimated shear wave propagation velocity is no lower than a predetermined velocity and transmits transmission detection waves at the second transmission interval during a period for which the estimated shear wave propagation velocity is lower than the predetermined velocity.

According to the above modification, detection waves are transmitted temporally densely during a period where shear wave velocity is high, and a decrease in accuracy of measurement of shear wave velocity is suppressed. Further, a long detection wave transmission interval is set for a period where shear wave velocity is low, and frequency of transmission of detection waves can be reduced.

(5) The ultrasound diagnostic device of (4) may be modified such that the push pulse transmitter transmits a plurality of push pulses, for each of the push pulses, following the transmission of the push pulse, the detection wave transmitter/receiver performs the transmission of transmission detection waves and the reception of reception detection waves, the displacement detector performs the detection of subject tissue displacement inside the ROI using receive signals acquired through the transmission of transmission detection waves and the reception of reception detection waves performed following the transmission of the push pulse, and the shear wave analyzer performs the detection of a shear wave propagation velocity inside the ROI based on the subject tissue displacement, and the shear wave analyzer combines detected shear wave propagation velocities and holds a result of the combining.

According to the above modification, accuracy of a result of shear wave propagation velocity analysis can be improved by combining shear wave propagation velocities. Further, a method of transmitting detection waves can be optimized based on a shear wave propagation velocity analysis result with high accuracy.

(6) The ultrasound diagnostic device of (4) may be modified such that the push pulse transmitter transmits a plurality of push pulses, for each of the push pulses, following the transmission of the push pulse, the detection wave transmitter/receiver performs the transmission of transmission detection waves and the reception of reception detection waves, the displacement detector performs the detection of subject tissue displacement inside the ROI using receive signals acquired through the transmission of transmission detection waves and the reception of reception detection waves performed following the transmission of the push pulse, and the shear wave analyzer performs the detection of a shear wave propagation velocity inside the ROI based on the subject tissue displacement, and holds the detected shear wave propagation velocity, and after all of the plurality of push pulses have been transmitted, the shear wave analyzer combines detected shear wave propagation velocities.

According to the above modification, accuracy of a result of shear wave propagation velocity analysis can be improved by combining shear wave propagation velocities. Further, a method of transmitting detection waves following transmission of one push pulse can be determined based on a result of analysis of a shear wave generated due to a previous push pulse. Accordingly, even when there is no combined propagation velocity for a same ROI, a transmission method of detection waves can be optimized.

(7) The ultrasound diagnostic device of (4) may be modified such that the detection wave transmitter/receiver, before the transmission of the subsequent push pulse, estimates a shear wave position based on the shear wave propagation velocity held by the shear wave analyzer, and after the transmission of the subsequent push pulse, transmits transmission detection waves only while the estimated shear wave position is inside the ROI.

According to the above modification, transmission and reception of unnecessary detection waves can be suppressed, and the number of times transmission/reception of detection waves is performed can be reduced without affecting accuracy of shear wave propagation velocity measurement.

(8) The ultrasound diagnostic device of (4) may be modified such that for the estimation of shear wave propagation velocity, the detection wave transmitter/receiver uses information regarding a depth of a focal point of the push pulse, the information included in the shear wave propagation velocity held by the shear wave analyzer.

(9) The ultrasound diagnostic device of (7) may be modified such that for the estimation of shear wave propagation velocity and shear wave position, the detection wave transmitter/receiver uses information regarding a depth of a focal point of the push pulse, the information included in the shear wave propagation velocity held by the shear wave analyzer.

According to the above modifications, shear wave velocity and position can be estimated efficiently.

INDUSTRIAL APPLICABILITY

The ultrasound diagnostic device and the ultrasound signal processing method pertaining to the present disclosure are useful for the measurement of tissue stiffness using ultrasound. The ultrasound diagnostic device and the ultrasound signal processing method thereby improve accuracy of tissue stiffness measurement and have high applicability to medical diagnostic equipment, etc.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound diagnostic device that uses an ultrasound probe to detect a shear wave propagation velocity of a shear wave generated at a specific part inside a subject by physically pushing tissue at the specific part by transmitting an ultrasound push pulse focusing on the specific part and then repeatedly transmitting and receiving ultrasound detection waves to and from inside the subject, the ultrasound diagnostic device comprising:

ultrasound signal processing circuitry, the ultrasound signal processing circuitry comprising:

a push pulse transmitter that transmits a push pulse towards the subject, wherein the push pulse generates the shear wave in the subject;

a detection wave transmitter/receiver that, following the transmission of the push pulse, transmits plane wave transmission detection waves towards a region of interest (ROI) inside the subject and receives reflection detection waves corresponding to the transmission detection waves from the subject, to generate receive signals sequentially for detecting the shear wave propagation velocity of the shear wave;

a displacement detector that detects, from the receive signals, subject tissue displacement occurring inside the ROI at time points of reception of the reflection detection waves due to the shear wave generated by the push pulse; and a shear wave analyzer that detects the shear wave propagation velocity inside the ROI based on the subject tissue displacement, wherein the transmission detection waves are transmitted following the push pulse according to a predetermined transmission profile that at least includes transmission detection waves transmitted by the detection wave transmitter/receiver at a first transmission interval during a first period following the push pulse and transmission detection waves transmitted by the detection wave transmitter/receiver at a second transmission interval during a second period following the first period, wherein the second transmission interval is longer than the first transmission interval, and each of the transmission detection waves transmitted during the first period and the transmission detection waves transmitted during the second period covers the entire ROI, the shear wave analyzer holds the shear wave propagation velocity, and the detection wave transmitter/receiver, after transmission of a subsequent push pulse, transmits transmission detection waves at the first transmission interval during a period over which an estimated shear wave propagation velocity is no lower than a predetermined velocity and transmits transmission detection waves at the second transmission interval during a period for which the estimated shear wave propagation velocity is lower than the predetermined velocity, wherein the estimated shear wave propagation velocity is based on the shear wave propagation velocity held by the shear wave analyzer.

2. The ultrasound diagnostic device of claim 1, wherein the detection wave transmitter/receiver transmits transmission detection waves at the first transmission interval until a total number of transmission detection waves transmitted since the transmission of the push pulse reaches a predetermined number and transmits transmission detection waves at the second transmission interval after the total number of transmission detection waves transmitted reaches the predetermined number.

3. The ultrasound diagnostic device of claim 1, wherein the push pulse transmitter transmits a plurality of push pulses, for each of the push pulses,
   following the transmission of the push pulse, the detection wave transmitter/receiver performs the transmission of transmission detection waves and the reception of reception detection waves,
   the displacement detector performs the detection of subject tissue displacement inside the ROI using receive signals acquired through the transmission of transmission detection waves and the reception of reception detection waves performed following the transmission of the push pulse, and
   the shear wave analyzer performs the detection of the shear wave propagation velocity inside the ROI based on the subject tissue displacement, and the shear wave analyzer combines detected shear wave propagation velocities and holds a result of the combining.

4. The ultrasound diagnostic device of claim 1, wherein the push pulse transmitter transmits a plurality of push pulses, for each of the push pulses,
   following the transmission of the push pulse, the detection wave transmitter/receiver performs the transmission of transmission detection waves and the reception of reception detection waves,
   the displacement detector performs the detection of subject tissue displacement inside the ROI using receive signals acquired through the transmission of transmission detection waves and the reception of reception detection waves performed following the transmission of the push pulse, and
   the shear wave analyzer performs the detection of the shear wave propagation velocity inside the ROI based on the subject tissue displacement, and holds the detected shear wave propagation velocity, and after all of the plurality of push pulses have been transmitted, the shear wave analyzer combines detected shear wave propagation velocities.

5. The ultrasound diagnostic device of claim 1, wherein the detection wave transmitter/receiver, after the transmission of the subsequent push pulse, transmits transmission detection waves only while an estimated shear wave position is inside the ROI, and the estimated shear wave position is based on the shear wave propagation velocity held by the shear wave analyzer.

6. The ultrasound diagnostic device of claim 5, wherein the estimated shear wave propagation velocity and the estimated shear wave position are further based on information regarding a depth of a focal point of the push pulse, which is held by the shear wave analyzer.

7. The ultrasound diagnostic device of claim 1, wherein the estimated shear wave propagation velocity is further based on information regarding a depth of a focal point of the push pulse, which is held by the shear wave analyzer.

8. The ultrasound diagnostic device of claim 1, wherein the predetermined transmission profile further includes transmission detection waves transmitted at a third transmission interval during a third period following the second period, and the third transmission interval is longer than the second transmission interval.

9. The ultrasound diagnostic device of claim 1, wherein the second period begins after the first period has ended, the first transmission detection waves consist of waves transmitted at the first transmission interval and the second transmission detection waves consist of waves transmitted at the second transmission interval.

10. The ultrasound diagnostic device of claim 1, wherein the displacement detector detects the subject tissue displacement based on tomographic image signals based on the receive signals.

11. An ultrasound signal processing method in which an ultrasound probe is used to detect a shear wave propagation velocity of a shear wave generated at a specific part inside a subject by physically pushing tissue at the specific part by transmitting an ultrasound push pulse focusing on the specific part and then repeatedly transmitting and receiving ultrasound detection waves to and from inside the subject, the ultrasound signal processing method comprising:

transmitting a push pulse towards the subject, the push pulse generating the shear wave in the subject;

following the transmission of the push pulse, transmitting plane wave transmission detection waves towards a region of interest (ROI) inside the subject and receiving reflection detection waves corresponding to the transmission detection waves from the subject, to generate receive signals sequentially for detecting the shear wave propagation velocity of the shear wave;

detecting, from the receive signals, subject tissue displacement occurring inside the ROI at time points of reception of the reflection detection waves due to the shear wave generated by the push pulse; and detecting by a shear wave analyzer the shear wave propagation velocity inside the ROI based on the subject tissue displacement, wherein the transmission detection waves are transmitted following the push pulse according to a predetermined transmission profile that at least includes transmission detection waves transmitted at a first transmission interval during a first period following the push pulse and transmission detection waves transmitted at a second transmission interval during a second period following the first period, wherein the second transmission interval is longer than the first transmission interval, and each of the transmission detection waves transmitted during the first period and the transmission detection waves transmitted during the second period covers the entire ROI, the shear wave propagation velocity is held in the shear wave analyzer, and after transmission of a subsequent push pulse, transmitting transmission detection waves at the first transmission interval during a period over which an estimated shear wave propagation velocity is no lower than a predetermined velocity and transmitting transmission detection waves at the second transmission interval during a period for which the estimated shear wave propagation velocity is lower than the predetermined velocity, wherein the estimated shear wave propagation velocity is based on the shear wave propagation velocity held by the shear wave analyzer.

* * * * *